United States Patent
Pritchard et al.

(10) Patent No.: US 9,670,486 B2
(45) Date of Patent: Jun. 6, 2017

(54) RNAI-BASED METHOD OF SCREENING AND CHARACTERIZING DRUG COMBINATIONS

(75) Inventors: Justin Pritchard, Boston, MA (US); Douglas A. Lauffenburger, Cambridge, MA (US); Michael Hemann, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 140 days.

(21) Appl. No.: 13/994,057

(22) PCT Filed: Dec. 16, 2011

(86) PCT No.: PCT/US2011/065630
§ 371 (c)(1),
(2), (4) Date: Dec. 13, 2013

(87) PCT Pub. No.: WO2012/083243
PCT Pub. Date: Jun. 21, 2012

(65) Prior Publication Data
US 2014/0206544 A1    Jul. 24, 2014

(51) Int. Cl.
*C12Q 1/68*     (2006.01)
*G01N 33/50*    (2006.01)
*C12N 15/10*    (2006.01)

(52) U.S. Cl.
CPC ....... *C12N 15/1079* (2013.01); *C12Q 1/6883* (2013.01); *C12Q 1/6886* (2013.01); *G01N 33/5023* (2013.01); *C12Q 2600/136* (2013.01); *C12Q 2600/178* (2013.01)

(58) Field of Classification Search
USPC ............ 435/6.1, 91.1, 375, 455, 6.11, 6.13, 435/91.31; 514/44, 1, 2; 536/23.1, 24.5; 424/9.1
See application file for complete search history.

(56) References Cited

U.S. PATENT DOCUMENTS

| | | | |
|---|---|---|---|
| 2005/0181385 A1 | 8/2005 | Linsley et al. | |
| 2010/0168022 A1 | 7/2010 | Centeno | |
| 2011/0054001 A1* | 3/2011 | Look et al. | 514/410 |
| 2011/0307427 A1 | 12/2011 | Linke et al. | |
| 2014/0134635 A1 | 5/2014 | Jiang et al. | |
| 2014/0206544 A1 | 7/2014 | Pritchard et al. | |

FOREIGN PATENT DOCUMENTS

WO   WO 2012/083231 A9   6/2012
WO   WO2012/083243 A1    6/2012

OTHER PUBLICATIONS

Jiang et al, Genes & Development, vol. 23, pp. 1895-1909 (2009)
Brummelkamp et al, Nature Chemical Biology, vol. 2, No. 4, pp. 202-206 (2006) Youle et al, Nature Reviews, Molecular Cell Biology, vol. 9, pp. 47-59 (2008). 2011/0054001.*
Brummelkamp et al, Nature Chemical Biology, vol. 2, No. 4, pp. 202-206 (2006).*
Youle et al, Nature Reviews, Molecular Cell Biology, vol. 9, pp. 47-59 (2008).*
Olsson et al, Cell Death and Differentiation, vol. 14, pp. 1561-1575 (2007).*
Erker et al, Human Molecular Genetics, vol. 14, No. 12, pp. 1699-1708 (2005).*
Chipoy et al, Oncogene, vol. 26, pp. 6653-6664 (2007).*
Adams, J.M., et al., "The C-MYC Oncogene Driven by Immunoglobulin Enhancers Induces Lymphoid Malignancy in Transgenic Mice", *Nature*, 318(6046): 533-538 (1985).
Akhtar, M.S., et al., "TFIIH Kinase Places Bivalent Marks on the Carboxy-Terminal Domain of RNA Polymerase II", *Molecular Cell*, 34: 387-393 (2009).
Bartek, J. and Lukas, J., "Chk1 and Chk2 Kinases in Checkpoint Control and Cancer", *Cancer Cell*. 3: 421-429 (2003).
Berns, K., et al., "A Large-Scale RNAi Screen in Human Cells Identifies New Components of the p53 Pathway", *Nature*, 428: 431-437 (2004).
Berns, K., et al., "A Large-Scale RNAi Screen in Human Cells Identifies New Components of the p53 Pathway: Supplementary Talbe 1 Genes in the NKI RNAi Library", *Nature*, 428: 7pages (2004).
Blanchard, J.S., "Molecular Mechanisms of Drug Resistance in *Mycobacterium tuberulosis*", *Annu. Rev. Biochem.*, 65: 215-239 (1996).
Bode, A.M. and Dong, Z., "Post-Translational Modification of p53 in Tumorigenesis", *Nature Reviews Cancer*, 4: 793-805 (2004).
Borisy, A.A., et al., "Systematic Discovery of Multicomponent Therapeutics", *PNAS*, 100(13): 7977-7982 (2003).
Brossier, F., et al., "Detection by GenOType MTBDRs/ Test of Complex Mechanisms of Resistance to Second-Line Drugs and Ethambutol in Multidrug-Resistant *Mycobacterium tuberculosis* Complex Isotates", *J. Clin. Microbiol.*, 48(5): 1683-1619 (2010).

(Continued)

*Primary Examiner* — Jane Zara
(74) *Attorney, Agent, or Firm* — Hamilton, Brook, Smith & Reynolds, P.C.

(57) ABSTRACT

In one aspect, the invention is directed to a method of characterizing a mechanism of action of a combination of agents. The method comprises contacting a plurality of populations of cells with a combination of agents to be assessed, wherein each population of cells have one gene of interest targeted by a small hairpin RNA (shRNA) and wherein the gene of interest regulates cell death and a plurality of genes that regulate cell death are targeted in the plurality of populations of cells. A responsiveness of each population of cells to the combination of agents is determined, thereby obtaining an shRNA signature of the combination of agents so as to identify one or more genes that mediate a response to the combination of agents, thereby characterizing the mechanism of action of the combination of agents. In another aspect, the invention is directed to a method of determining whether a patient population treated with a first agent would benefit from a treatment using the first agent in combination with one or more additional agents. In yet another aspect, the invention is directed to method of determining whether a formulation of one or more agents maintains a mechanism of action of the one or more agents when unformulated.

27 Claims, 21 Drawing Sheets

(56) References Cited

OTHER PUBLICATIONS

Brumbaugh, K.M., et al., "The mRNA Surveillance Protein hSMG-1 Fucntions in Genotoxic Stress Response Pathways in Mammalian Cells", *Molecular Cell*, 14: 585-598 (2004).

Brummelkamp, T., et al., "An shRNA Barcode Screen Provides Insight Into Cancer Cell Vulnerability to MDM2 Inhibitors", *Nature Chemical Biology*, 2(4): 202-206 (2006).

Budman, D.R., et al., "Dose and Dose Intensity as Determinants of Outcome in the Adjuvant Treatment of Breast Cancer", *J. National Cancer Institute*, 90(16): 1205-1211 (1998).

Burgess, D.J., et al., "Topoisomerase Levels Determine Chemotherapy Response In Vitro and In Vivo", *PNAS*, 105(26): 9053-9058 (2008).

Carbone, P.P, et al., "Management of Patients With Malignant Lymphoma" A Comparative Study With Cyclophosphamide and Vinca Alkaloids, *Cancer Research*, 28(5): 811-822 (1968).

Chen, G., et al., "Prevalence of Multidrug Resistance Related to Activation of the mdr1 Gene in Human Sarcoma Mutants Derived by Single-Step Doxorubicin Selection", *Cancer Research*, 54: 4980-4927 (1994).

Chen, G., et al., "MDR1 Activation is the Predominant Resistance Mechanism Selected by Vinblastine in MES-SA Cells", *British Journal of Cancer*, 83(7): 892-898 (2000).

Cimprich, K.A. and Cortez, D., "ATR: An Essential Regulator of Genome Integrity", *Nature Rev. Mol. Cell Biol.*, 9: 616-627 (2008).

DeVita, V.T. and Schein, P.S., "The Use of Drugs in Combination for the Treatment of Cancer: Rationale and Results", *N.Engl. J. Med.*, 288(19): 998-1006 (1973).

Dickins, R.A., et al., "Probing Tumor Phenotypes Using Stable and Regulated Synthetic mircroRNA Precursors", *Nature Genetics*, 37(11): 1289-1295 (2005).

Frei, III, E., "Curative Cancer Chemotherapy", *Cancer Research*, 45: 6523-6537 (1985).

Frei, III, E., et al., "A Comparative Study of Two Regimens of Combination Chemotherapy in Acute Leukemia", *Blood*, 13: 1126-1148 (1958).

Frei, III, E., et al., "The Relationship Between High-Dose Treatment and Combination Chemotherapy: The Concept of Summation Dose Intensity", *Clin. Cancer Res.*, 4: 2027-2037 (1998).

Gardner, T.S., et al., "Inferring Genetic Networks and Identifying compound Mode of Action via Expression Profiling", *Science*, 301: 102-105, (2003).

Giaever, G., et al., "Genomic Profliling of Drug Sensitivities via Induced Haploinsufficiency", *Nature Genetics*, 21: 278-253 (1999).

Giaever, G., et al., "Chemogenomic Profiling: Identifying the Functional Interactions of Small Molecules in Yeast", *PNAS*, 101(3): 793-798 (2004).

Goldin, A. and Mantel, N., "The Employment of Combinations of Drugs in the Chemotherapy of Neoplasia: A Review", *Cancer Research*, 17(7): 635-654 (1957).

Goldin, A., et al., "Factors Influencing Antitumor Synergism: Relation to Screening Methodology", *Annals of the NY Acad. of Sciences*, 76: 932-938 (1958).

Greco, W.R., et al., "The Search for Cytotoxic Synergy Between Anticancer Agents: A Case of Dorothy and The Ruby Slippers?", *J. of the National Cancer Institute*, 88(11): 699-700 (1996).

Hieronymus, H., et al., "Gene Expression Signature-Based Chemical Genomic Prediction Identifies a Novel Class of HSP90 Pathway Modulators", *Cancer Cell*, 10: 321-330 (2006).

Hillenmeyer, M.E., et al., "The Chemical Genomic Portrait of Yeast: Uncovering a Phenotype for All Genes", *Science*, 320: 362-365 (2008).

Hillenmeyer, M.E., et al., "Systematic Analysis of Genome-Wide Fitness DAta in Yeast Reveals Novel Gene Function and Drug Action", *Genome Biology*, 11: R30, 17pages (2010).

Ho, C.H., et al., "A Molecular Barcoded Yeast ORF Library Enables Mode-of-Action Analysis of Bioactive Compounds", *Nature Biotechnol.*, 27(4): 369-377 (2009).

Huel, T., et al., "Distinguishing Rational From Irrational Applications of Pharmacogenetic Synergies From the Bench to Clinical Trials", *Cell Cycle*, 6(11): 1336-1341 (2007).

Hughes, T.R., et al., "Functinal Discovery via a Compendium of Expression Profiles", *Cell*, 102: 109-126 (2000).

Iorns, E., et al., "Utilizing RNA Interference to Enhance Cancer Drug Discovery", *Nature Reviews Drug Discovery*, 6: S56-S68 (2007).

Jiang, H., et al., "The Combined Status of ATM and p53 Link Tumor Development With Therapeutic Response", *Genes & Development*, 23: 1895-1909 (2009).

Jiang, H., et al., "A Mammalian Functional-Genetic Approach to Characterizing Cancer Therapeutics", *Nat. Chem. Biol.*, 7(2): 92-100 (2011).

Krutzik, P.O., et al., "High Content Single-Cell Drug Screening With Phosphospecific Flow Cytometry", *Nat. Chem. Biol.*, 4(2): 132-142 (2008).

Lamb, J., et al., "The Connectivity Map: Using Gene-Expression Signatures to Connect Small Molecules, Genes, and Disease", *Science*, 313: 1929-1935 (2006).

Lau, D.H.M., et al., "Multifactorial Mechanisms Associated With Broad Cross-Resistance of Ovarian Carcinoma Cells Selected by Cyanomorpholino Doxorubicin",*Cancer Research*, 51: 5151-5187 (1991).

Lavin, M.F., "Ataxia-Telangiectasia: From a Rare Disorder to a Paradigm for Cell Signalling and Cancer", *Nature Reviews Molecular Cell Biology*, 9: 759-769 (2008).

Law, L.W., "Effects of Combinations of Antileukemic Agents on an Acute Lymphocytic Leukemia of Mice", *Cancer Research*, 12: 871-878 (1952).

Law, L.W., "Origin of the Resistance of Leukaemic Cells to Folic Acid Antagonists", *Nature*, 169: 628-629 (1952).

Lehár, J., et al., "Synergistic Drug Combinations Tend to Improve Therapeutically Relevant Selectivity", *Nature Biotechnol.*, 27: 659-666 (2009).

Lindemann, R.K., et al., "Analysis of the Apoptotic and Therapeutic Activities of Histone Deacetylase Inhibitors by Using a Mouse Model of B Cell Lymphoma", *PNAS*, 104(19): 8071-8076 (2007).

Ljungman, M. and Paulsen, M.T., "The Cyclin-Dependent Kinase Inhibitor Roscovitine Inhibits RNA Synthesis and Triggers Nuclear Accumulation of p53 That Is Unmodified at Ser15 and Lys382", *Molecular Pharmacology*, 60(4): 785-789 (2001).

Longley, D.B., et al., "5-Flourouracil: Mechanisms of Action and Clinical Strategies", *Nat. Rev. Cancer*, 3(5): 330-338 (2003).

Lowe, S.W., et al., "p53-Dependent Apoptosis Modulates the Cytotoxicity of Anticancer Agents", *Cell*, 74(6): 957-967 (1993).

Lowe, S.W., et al., "p53 Status and the Efficacy of Cancer Therapy In Vivo", *Science*, 266: 807-810 (1994).

Lu, C. and El-Deiry, W.S., "Targeting p53 for Enhanced Radio- and Chemo-Sensitivity", *Apoptosis*, 14(4): 597-606 (2009).

Lum, P.Y., et al., "Discovering Modes of Action for Therapeutic Compounds Using a Genome-Wide Screen of Yeast Heterozygotes", *Cell*, 116: 121-137 (2004).

Luria, S.E. and Delbrück, M., "Mutations of Bacteria From Virus Sensitivity to Virus Resistance", *Genetics*, 28: 491-511 (1943).

MacCallum, D.E., et al., "Seliciclib (CYC202, R-Roscovitine) Induces Cell Death in Multiple Myeloma Cells by Inhibition of RNA Polymerase II-Dependent Transcription and Down-Regulation of Mcl-1", *Cancer Resarch*, 65(12): 5399-5407 (2005).

Mojas, N., et al., "Mismatch Repair-Dependent Processing of Methylation Damage Gives Rise to Persistent Single-Stranded Gaps in Newly Replicated DNA", *Genes Dev.*, 21: 3342-3355 (2007).

Mullenders, J., et al., "Candidate Biomarkers of Response to an Experimental Cancer Drug Identified Through a Large-Scale RNA Interference Genetic Screen", *Clinical Cancer Research*, 15(18): 5811-5819 (2009).

Mullighan, C.G., et al., "Genomic Analysis of the Clonal Origins of Relapsed Acute Lyphoblastic Leukemia", Science, 322: 1377-1380 (2008).

Newcombe, H.B. and Nyholm, M.H., "The Inheritance of Streptomycin Resistance and Dependence in Crosses of *Escherichia coli*", *Genetics*, 35: 603-611 (1950).

(56) References Cited

OTHER PUBLICATIONS

Parsons, A.B., et al., "Integration of Chemical-Genetic and Genetic Interaction Data Links Bioactive Compounds to Cellular Target Pathways", *Nature Biotechnology*, 22(1): 62-69 (2004).
Parsons, A.B., et al., "Exploring the Mode-of-Action of Bioactive Compounds by Chemical-Genetic Profiling in Yeast", *Cell*, 126: 611-625 (2006).
Pearce, A.K. and Humphrey, T.C., "Integrating Stress-Response and Cell-Cycle Checkpoint Pathways", *Trends in Cell Biology*, 11(10): 426-433 (2001).
Perlman, Z.E., et al., "Multidimensional Drug Profiling by Automated Microscopy", *Science*, 306: 1194-1198 (2004).
Pritchard, J.R., et al., "Thre-Kinase Inhibitor Combination Recreates Multipathway Effects of a Geldanamycin Analogue on Hepatocellular Carcinoma Cell Death", *Mol Cancer Ther*, 8: 2183-2192 (2009).
Ramalingam, S.S., et al., "A Phase 1 Study of 17-Allylamino-17-Demethoxygeldanamycin Combined with Paclitaxel in Patients With Advanced Solid Malignancies", *Clin. Cancer Res.*, 14(11): 3456-3461 (2008).
Reinhardt, H.C., et al., "p53-Deficient Cells Rely on ATM-andATR-Mediated Checkpoint Signaling Through the p38MAPK/MK2 Pathway for Survival After DNA Damage", *Cancer Cell*, 11: 175-189 (2007).
Rihel, J., et al., "Zebrafish Behavioral Profiling Links Drugs to Biological Targets and Rest/Wake Regulation", *Science*, 327: 348-351 (2010).
Sato, S., et al., "Biochemical Target Isolation for Novices: Affinity-Based Strategies", *Chemistry & Biology*, 17: 616-623 (2010).
Schmitt, C.A., et al., "INK4α/ARF Mutations Accelerate Lymphomagenesis and Promote Chemoresistance by Disabling p53", *Genes & Development*, 13: 2670-2677 (1999).
Shoemaker, R.H., "The NCI60 Human Tumour Cell Line Anticancer Drug Screen", *Nature Review Cancer*, 6: 813-823 (2006).
Skipper, H.E., et al., Experimental Evaluation of Potential Anticancer Agents. *Cancer Chemotherapy Reports Part I*, 35: 1-111 (1964).
Suzuki R. and Shimodaira, H., "Pvclust: An R Package for Assessing the Uncertainty in Hierarchical Clustering", *Bioinformatics*, 22(12): 1540-1542 (2006).
Swann, P.F., et al., "Role of Postreplicative DNA Mismatch Repair in the Cytotoxic Action of Thioguanine", *Science*, 273: 1109-1111 (1996).
Telenti, A., et al., "Detection of Rifampican-Resistance Mutations in *Mycobacterium tuberculosis*", *Lancet*, 341(8846): 647-650 (1993).
Weinstein, J.N., et al., "An Information-Intensive Approach to the Molecular Pharmacology of Cancer", *Science*, 275: 343-349 (1997).
Whitehurst, A.W., et al., "Synthetic Lethal Screen Identification of Chemosensitizer Loci in Cancer Cells", *Nature*, 446: 815-819 (2007).
Williams, R.T., et al., "Arf Gene Loss Enhances Oncogenicity and Limits Imatinib Response in Mouse Models of Ber-Ab1-Induced Acute Lymphoblastic Leukemia", *PNAS*, 103(17): 6688-6693 (2006).
Youle, R. J. and Strasser, A., "The BCL-2 Protein Family: Opposing Activities That Mediate Cell Death", *Nature Reviews Molecular Cell Biology*, 9: 47-59 (2008).
Notification of Transmittal of the International Search Report and the Written Opinion of the International Searching Authority for PCT/US2011/065611, "RNAi-Based Method of Drug Screening and Characterization"; date of mailing May 30, 2012.
Notification of Transmittal of the International Search Report and the Written Opinion of the International Searching Authority for PCT/US2011/065630, "RNAi-Based Method of Drug Screening and Characterization"; date of mailing May 23, 2012.
International Preliminary Report on Patentability for PCT/US2011/065611, RNAi-Based Method of Drug Screening and Characterization; date of issuance Jun. 18, 2013.
International Preliminary Report on Patentability for PCT/US2011/065630, RNAi-Based Method of Drug Screening and Characterization; date of issuance Jun. 18, 2013.
Non-Final Office Action for U.S. Appl. No. 13/993,930, "RNAi-Based Method of Drug Screening and Characterization", date of mailing Oct. 23, 2015.
Assinder, S.J., et al., "The TGF-β, PI3K/Akt and PTEN Pathways: Established and Proposed Biobhemical Integrations in Prostate Cancer", Biochem. J., 417:411-421 (2009).
Awuah, S.G., et al., "A Platinum(IV) Pro-Drug Preferentially Targets IDO Providing Enhanced Ovarian Cancer Immuno-Chemotherapy", *J Am Chem Soc.*, 137(47):14854-14857 (2015).
Paddison, P.J., et al., "Short Hairpin RNAs (shRNAs) Induce Sequence-Specific Silencing in Mammalian Cells", *Genes & Development*, 16: 948-958 (2002).
Pritchard, J.R., et al., "Defining Principles of Combination Drug Mechanisms of Action", *PNAS*, E170-E179 (2012).
Suntharalingam, K., et al., "Bidentate Ligands on Osmium(VI) Nitrido Complexes Control Intracellular Targeting and Cell Death Pathways", *J Am Chem Soc.*, 135(38):14060-14063 (2013).
Suntharalingam, K., et al., "A Breast Cancer Stem Cell-Selective, Mammospheres-Potent Osmium(VI) Nitrido Complex", *J Am Chem Soc*, 136:14413-14416 (2014).
Suntharalingam, K., et al., "Necroptosis-Inducing Rhenium(V) Oxo Complexes", *J Am Chem Soc*, 137(8):2967-2974 (2015).
Zhao, B., et al., "Addressing Genetic Tumor Heterogeneity Through Computationally Predictive Combination Therapy", *Cancer Discov.*, 4(2):166-174 (2014).
Non-Final Office Action for U.S. Appl. No. 13/993,930, "RNAi-Based Method of Drug Screening and Characterization," date of mailing Jun. 10, 2016.
Notice of Allowance for U.S. Appl. No. 13/993,930, Date Mailed: Jan. 18, 2017.

* cited by examiner

1a

1b

5a

5b

SEQUENCE LISTING

```
<160> NUMBER OF SEQ ID NOS: 35

<210> SEQ ID NO 1
<211> LENGTH: 21
<212> TYPE: DNA
<213> ORGANISM: Unknown
<220> FEATURE:
<223> OTHER INFORMATION: shRNA target sequence for p53

<400> SEQUENCE: 1
ccactacaag tacatgtgta a                                              21

<210> SEQ ID NO 2
<211> LENGTH: 21
<212> TYPE: DNA
<213> ORGANISM: Unknown
<220> FEATURE:
<223> OTHER INFORMATION: shRNA target sequence for p53

<400> SEQUENCE: 2
tggagagtat ttcaccctca a                                              21

<210> SEQ ID NO 3
<211> LENGTH: 21
<212> TYPE: DNA
<213> ORGANISM: Unknown
<220> FEATURE:
<223> OTHER INFORMATION: shRNA target sequence for ATM

<400> SEQUENCE: 3
cacgaagtcc tcaataatct a                                              21
```

```
<210> SEQ ID NO 4
<211> LENGTH: 21
<212> TYPE: DNA
<213> ORGANISM: Unknown
<220> FEATURE:
<223> OTHER INFORMATION: shRNA target sequence for ATM

<400> SEQUENCE: 4
cagaaacaca taatcattaa a                                              21

<210> SEQ ID NO 5
<211> LENGTH: 21
<212> TYPE: DNA
<213> ORGANISM: Unknown
<220> FEATURE:
<223> OTHER INFORMATION: shRNA target sequence for Chk2

<400> SEQUENCE: 5
cactttcact atgtagaaat a                                              21

<210> SEQ ID NO 6
<211> LENGTH: 21
<212> TYPE: DNA
<213> ORGANISM: Unknown
<220> FEATURE:
<223> OTHER INFORMATION: shRNA target sequence for Chk2

<400> SEQUENCE: 6
acccatgttc ttgacattga a                                              21

<210> SEQ ID NO 7
<211> LENGTH: 21
<212> TYPE: DNA
<213> ORGANISM: Unknown
<220> FEATURE:
<223> OTHER INFORMATION: shRNA target sequence for ATR

<400> SEQUENCE: 7
acctttaatg agtgtcttaa a                                              21

<210> SEQ ID NO 8
<211> LENGTH: 21
<212> TYPE: DNA
<213> ORGANISM: Unknown
<220> FEATURE:
<223> OTHER INFORMATION: shRNA target sequence for ATR

<400> SEQUENCE: 8
caggaatatt ctgattggaa a                                              21

<210> SEQ ID NO 9
<211> LENGTH: 21
<212> TYPE: DNA
<213> ORGANISM: Unknown
<220> FEATURE:
<223> OTHER INFORMATION: shRNA target sequence for Chk1

<400> SEQUENCE: 9
aagggcttga ccaattataa a                                              21

<210> SEQ ID NO 10
<211> LENGTH: 42
<212> TYPE: DNA
<213> ORGANISM: Unknown
<220> FEATURE:
<223> OTHER INFORMATION: shRNA target sequence for Smg1
```

```
<400> SEQUENCE: 10
caggatagca ataaagatga acaggctgca ttcataact ta                    42

<210> SEQ ID NO 11
<211> LENGTH: 42
<212> TYPE: DNA
<213> ORGANISM: Unknown
<220> FEATURE:
<223> OTHER INFORMATION: shRNA target sequence for DNA-PKcs

<400> SEQUENCE: 11
caggcctata cttacagtta actccaacat gtagagaaca aa                   42

<210> SEQ ID NO 12
<211> LENGTH: 21
<212> TYPE: DNA
<213> ORGANISM: Unknown
<220> FEATURE:
<223> OTHER INFORMATION: shRNA target sequence for JNK1

<400> SEQUENCE: 12
tcagagcata acaaacttaa a                                          21

<210> SEQ ID NO 13
<211> LENGTH: 21
<212> TYPE: DNA
<213> ORGANISM: Unknown
<220> FEATURE:
<223> OTHER INFORMATION: shRNA target sequence for p38

<400> SEQUENCE: 13
caggtcttgt gtttaggtca a                                          21

<210> SEQ ID NO 14
<211> LENGTH: 21
<212> TYPE: DNA
<213> ORGANISM: Unknown
<220> FEATURE:
<223> OTHER INFORMATION: shRNA target sequence for A1

<400> SEQUENCE: 14
ggaagatggc ttcataaaga a                                          21

<210> SEQ ID NO 15
<211> LENGTH: 21
<212> TYPE: DNA
<213> ORGANISM: Unknown
<220> FEATURE:
<223> OTHER INFORMATION: shRNA target sequence for Bclb

<400> SEQUENCE: 15
aaggaatccc ttgaaaccta a                                          21

<210> SEQ ID NO 16
<211> LENGTH: 21
<212> TYPE: DNA
<213> ORGANISM: Unknown
<220> FEATURE:
<223> OTHER INFORMATION: shRNA target sequence for Bclw

<400> SEQUENCE: 16
ggctataagc tgaggcagaa g                                          21

<210> SEQ ID NO 17
```

```
<211> LENGTH: 21
<212> TYPE: DNA
<213> ORGANISM: Unknown
<220> FEATURE:
<223> OTHER INFORMATION: shRNA target sequence for Bclx

<400> SEQUENCE: 17
ggagagcgtt cagtgatcta a                                              21

<210> SEQ ID NO 18
<211> LENGTH: 21
<212> TYPE: DNA
<213> ORGANISM: Unknown
<220> FEATURE:
<223> OTHER INFORMATION: shRNA target sequence for Bad

<400> SEQUENCE: 18
cgcgagaaac gtgctttata a                                              21

<210> SEQ ID NO 19
<211> LENGTH: 21
<212> TYPE: DNA
<213> ORGANISM: Unknown
<220> FEATURE:
<223> OTHER INFORMATION: shRNA target sequence for Bak

<400> SEQUENCE: 19
ccggaaccta tgattacttg a                                              21

<210> SEQ ID NO 20
<211> LENGTH: 21
<212> TYPE: DNA
<213> ORGANISM: Unknown
<220> FEATURE:
<223> OTHER INFORMATION: shRNA target sequence for Bax

<400> SEQUENCE: 20
ccgcgtggtt gccctcttct a                                              21

<210> SEQ ID NO 21
<211> LENGTH: 21
<212> TYPE: DNA
<213> ORGANISM: Unknown
<220> FEATURE:
<223> OTHER INFORMATION: shRNA target sequence for Bid

<400> SEQUENCE: 21
cacagaagat tccatatcaa a                                              21

<210> SEQ ID NO 22
<211> LENGTH: 21
<212> TYPE: DNA
<213> ORGANISM: Unknown
<220> FEATURE:
<223> OTHER INFORMATION: shRNA target sequence for Bik

<400> SEQUENCE: 22
ccggacaggt gtcagaggta t                                              21

<210> SEQ ID NO 23
<211> LENGTH: 21
<212> TYPE: DNA
<213> ORGANISM: Unknown
<220> FEATURE:
<223> OTHER INFORMATION: shRNA target sequence for Bik

<400> SEQUENCE: 23
```
taggaacaga gaaatatgca a                                              21

<210> SEQ ID NO 24
<211> LENGTH: 21
<212> TYPE: DNA
<213> ORGANISM: Unknown
<220> FEATURE:
<223> OTHER INFORMATION: shRNA target sequence for Bim

<400> SEQUENCE: 24
caccctcaaa tggttatctt a                                              21

<210> SEQ ID NO 25
<211> LENGTH: 21
<212> TYPE: DNA
<213> ORGANISM: Unknown
<220> FEATURE:
<223> OTHER INFORMATION: shRNA target sequence for Bmf

<400> SEQUENCE: 25
cgcagagccc tggcatcaca a                                              21

<210> SEQ ID NO 26
<211> LENGTH: 21
<212> TYPE: DNA
<213> ORGANISM: Unknown
<220> FEATURE:
<223> OTHER INFORMATION: shRNA target sequence for Bnip3l

<400> SEQUENCE: 26
ggtatcagac tggtccagta g                                              21

<210> SEQ ID NO 27
<211> LENGTH: 21
<212> TYPE: DNA
<213> ORGANISM: Unknown
<220> FEATURE:
<223> OTHER INFORMATION: shRNA target sequence for Bclg

<400> SEQUENCE: 27
tccaaacagc atagagttca a                                              21

<210> SEQ ID NO 28
<211> LENGTH: 21
<212> TYPE: DNA
<213> ORGANISM: Unknown
<220> FEATURE:
<223> OTHER INFORMATION: shRNA target sequence for Bclg

<400> SEQUENCE: 28
ctggcctctg tgactgctct a                                              21

<210> SEQ ID NO 29
<211> LENGTH: 21
<212> TYPE: DNA
<213> ORGANISM: Unknown
<220> FEATURE:
<223> OTHER INFORMATION: shRNA target sequence for Bok

<400> SEQUENCE: 29
tcggtgtcca gccctagaga a                                              21

<210> SEQ ID NO 30
<211> LENGTH: 21
<212> TYPE: DNA

```
<213> ORGANISM: Unknown
<220> FEATURE:
<223> OTHER INFORMATION: shRNA target sequence for BPR

<400> SEQUENCE: 30
cccagcctct tccgagttct a                                         21

<210> SEQ ID NO 31
<211> LENGTH: 21
<212> TYPE: DNA
<213> ORGANISM: Unknown
<220> FEATURE:
<223> OTHER INFORMATION: shRNA target sequence for Hrk

<400> SEQUENCE: 31
cagcagggag tgtctacttt a                                         21

<210> SEQ ID NO 32
<211> LENGTH: 21
<212> TYPE: DNA
<213> ORGANISM: Unknown
<220> FEATURE:
<223> OTHER INFORMATION: shRNA target sequence for Mil1

<400> SEQUENCE: 32
cctgaagaag tgaagagctt a                                         21

<210> SEQ ID NO 33
<211> LENGTH: 21
<212> TYPE: DNA
<213> ORGANISM: Unknown
<220> FEATURE:
<223> OTHER INFORMATION: shRNA target sequence for Mule

<400> SEQUENCE: 33
ccacctcagc tacttcaagt t                                         21

<210> SEQ ID NO 34
<211> LENGTH: 21
<212> TYPE: DNA
<213> ORGANISM: Unknown
<220> FEATURE:
<223> OTHER INFORMATION: shRNA target sequence for Noxa

<400> SEQUENCE: 34
cagattgaat agtatgtgat a                                         21

<210> SEQ ID NO 35
<211> LENGTH: 24
<212> TYPE: DNA
<213> ORGANISM: Unknown
<220> FEATURE:
<223> OTHER INFORMATION: shRNA target sequence for Puma

<400> SEQUENCE: 35
ctgtagatat actggaatga avvv                                      24
```

RNAI-BASED METHOD OF SCREENING AND CHARACTERIZING DRUG COMBINATIONS

GOVERNMENT SUPPORT

This invention was made with Government support under Grant Nos. R01 CA128803 and U54 CA112967 awarded by the National Institutes of Health. The Government has certain rights in the invention.

RELATED APPLICATION(S)

This application is the U.S. National Stage of International Application No. PCT/US2011/065630, filed Dec. 16, 2011, which designates the U.S., published in English, and claims the benefit of U.S. Provisional Application No. 61/423,975, filed on Dec. 16, 2010.

The entire teachings of the above application(s) are incorporated herein by reference.

INCORPORATION BY REFERENCE OF MATERIAL IN ASCII TEXT FILE

This application incorporates by reference the Sequence Listing contained in the following ASCII text file:
a) File name: 00502179004SEQLIST.txt; created Dec. 31, 2013, 7 KB in size

BACKGROUND OF THE INVENTION

Combination chemotherapy is the standard of care for most disseminated cancers. Yet, despite the widespread use of these drug regimens, the basic mechanisms of combinatorial efficacy remain poorly understood. A common rationale for multi-drug administration in cancer is to evade spontaneous resistance to single agents, a model borrowed from microbiology, whereby multiple independent mutations in distinct drug targets are necessary to develop resistance (Luria, S. E. & Delbruck, M. Genetics 28, 491-511 (1943); Newcombe, H. B. & Nyholm, M. H. Genetics 35, 603-611 (1950); Law, L. W. Nature 169, 628-629 (1952); Law, L. W. Cancer Research 12, 871-878 (1952); Frei, E., 3rd et al. Blood 13, 1126-1148 (1958)). These arguments are well substantiated in drug resistant bacteria (Blanchard, J. S. Annual Review of Biochemistry 65, 215-239 (1996); Telenti, A. et al. Lancet 341, 647-650 (1993); Brossier, F., et al., Journal of Clinical Microbiology 48, 1683-1689 (2010)), but insufficient to explain the frequency of single mutations conferring multi-drug resistance in human cancers (Mullighan, C. G. et al. Science 322, 1377-1380 (2008); Chen, G., et al., Cancer Research 54, 4980-4987 (1994); Lau, D. H., et al. Cancer Research 51, 5181-5187 (1991); Chen, G. K., British Journal of Cancer 83, 892-898, (2000)). Synergistic cytotoxicity is also argued as a rationale for combination therapy (Goldin, A. & Mantel, N. Cancer Research 17, 635-654 (1957); Borisy, A. A. et al. Proc Natl Acad Sci USA 100, 7977-7982 (2003); Lehar, J. et al. Nature Biotechnology 27, 659-666 (2009)), but cell-intrinsic drug synergy frequently fails to predict efficacy in clinical trials (Goldin, A. & Mantel, N. Cancer Research 17, 635-654 (1957); Greco, W. R., et al., Journal of the National Cancer Institute 88, 699-700 (1996); Ramalingam, S. S. et al. Clinical Cancer Research 14, 3456-3461 (2008); Goldin, A., et al., Annals of the New York Academy of Sciences 76, 932-938 (1958)).

Thus a need exists for improved methods for understanding the mechanisms of combinatorial efficacy of drugs.

SUMMARY OF THE INVENTION

In one aspect, the invention is directed to a method of characterizing a mechanism of action of a combination of agents. The method comprises contacting a plurality of populations of cells with a combination of agents to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the combination of agents is determined, thereby obtaining an shRNA signature of the combination of agents so as to identify one or more genes that mediate a response to the combination of agents, thereby characterizing the mechanism of action of the combination of agents.

In another aspect, the invention is directed to a method of determining whether a patient population treated with a first agent would benefit from a treatment using the first agent in combination with one or more additional agents. The method comprises contacting a plurality of populations of cells with a combination of agents to be assessed wherein the combination comprises the first agent and one or more additional agents, and wherein each population of cells have one gene of interest targeted by a small hairpin RNA (shRNA), said gene of interest regulates cell death and a plurality of genes that regulate cell death are targeted in the plurality of populations of cells. A responsiveness of each population of cells to the combination of agents is determined, thereby obtaining an shRNA signature of the agent so as to identify one or more genes that mediate a response to the combination of agents. The shRNA signature of the combination of agents is compared to the shRNA signature of the first agent, wherein if the shRNA signature of the combination of agents is similar to the shRNA signature of the first agent, then the patient population treated with the first agent would benefit from a treatment using the first agent in combination with the one or more additional agents.

In yet another aspect, the invention is directed to method of determining whether a formulation of one or more agents maintains a mechanism of action of the one or more agents when unformulated. The method comprises contacting a plurality of populations of cells with a formulation of the one or more agents to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the formulation of the one or more agents is determined, thereby obtaining an shRNA signature of the formulation of the one or more agents so as to identify one or more genes that mediate a response to the formulation of the one or more agents. The shRNA signature of the formulation of the one or more agents is compared to the shRNA signature of the one or more agents when unformulated wherein if the shRNA signature of the formulation of the one or more agents is similar to the shRNA signature of the one or more agents when unformulated, then the formulation maintains the mechanism of action of the one or more agents when unformulated.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
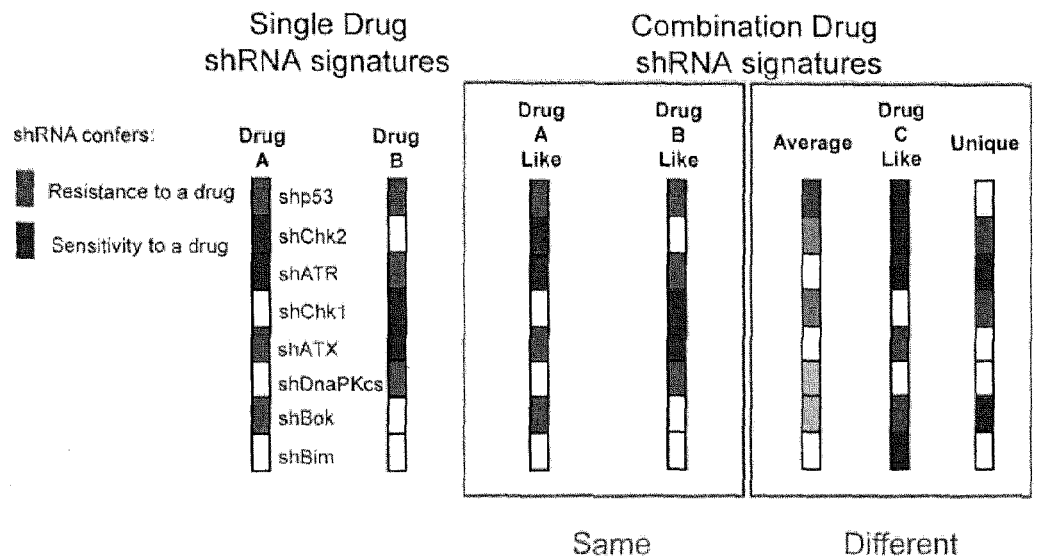
FIGS. 1a-1d: A strategy to define combination mechanisms of drug action. (1a) An illustration of the competing hypotheses for single versus combination mechanisms. Squares denote a diagrammatic version of an shRNA signature with resistance shown in red and sensitivity in blue. A schematic of the potential results following the combinations of Drugs A and B is shown to the right. "Same mechanism" refers to the idea that a combination signature could look similar to the individual drugs used to create the combination. The different mechanism box gives examples of how combination signatures might differ from component signatures. (1b) An outline of our signature based methodology. shRNAs targeting the 8 genes in our signature are retrovirally transduced in a mixed pool. These pools are subsequently treated with combinations of drugs and compared to a high resolution single drug signature dataset. (1c) A description of the process of comparing drug categories in our reference set. (1) The initial drug category size in the reference set is defined. (2) Out of category drugs are used as negative controls. These drugs are forced to belong to the wrong category. Iteration through the all of the negative controls produces a background distribution of how unrelated drugs affect category size. (3) Given a category prediction by the nearest neighbors algorithm, the category size is calculated, and (4) compared to the background distribution from (2). (1d) Top: A heatmap of the dose response of Eµ-Myc;p19Arf-/- to 5-FU with or without leucovorin. Bottom: an 8shRNA signature heatmap for 5-FU and 5-FU plus leucovorin measured concurrently at the indicated (starred) doses of cell killing. Linkage ratios and p-values are indicated below. 8-shRNA signatures for gemcitabine (Gem) and hydroxyurea (HU) are shown to aid interpretation.

A description of example embodiments of the invention follows.

Described herein is use of RNAi-based functional signatures in mammalian cells to test specific hypotheses underlying combination drug mechanisms. Shown herein is that while potently synergistic drug combinations reinforce the cytotoxic action of one component in a manner that highlights drug-specific genetic dependencies, clinically used multi-drug regimens minimize the effect of genetic diversity and thus homogenize response across distinct subpopulations. This finding was confirmed in spontaneously arising lymphomas, where standard combination therapy reduced the variation in drug response between different tumors. Thus, shown herein is that commonly used chemotherapeutic drug combinations are intrinsically "de-personalized" and function by homogenizing therapeutic response across randomized patient cohorts.

Accordingly, in one aspect, the invention is directed to a method of characterizing a mechanism of action of a combination of agents. The method comprises contacting a plurality of populations of cells with a combination of agents to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the combination of agents is determined, thereby obtaining an shRNA signature of the combination of agents so as to identify one or more genes that mediate a response to the combination of agents, thereby characterizing the mechanism of action of the combination of agents.

As will be appreciated by those of skill in the art, the mechanism of action of a variety of combinations of agents can be characterized using the methods described herein. For example, the agent can be a chemical compound, a nucleic acid, a peptide (a protein), a lipid, a sugar (e.g., polysaccharide), a lipopolysaccharide and the like and combinations thereof. In one aspect, the combination of agents is a combination of chemotherapeutic agents. In another aspect, the agent is a combination of genotoxic agents. In yet other aspects, the combination of agents is a combination of derivatives of one or more chemotherapeutic or genotoxic agents.

There are a variety of mechanisms of action by which agents (e.g., chemotherapeutic agents) exert their effects. Examples of mechanisms of action of a chemotherapeutic agent include inhibition of a topoisomerase, cross linking of DNA, inducement of single stand break of DNA, inhibition of nucleic acid synthesis, inhibition of mitosis, inhibition of RNA transcription, inhibition of histone modification enzymes, inhibition of heat shock proteins (e.g., Hsp90), alkylation of DNA, inhibition of proteasomes inducement of apoptosis or the like. The methods described herein can further comprise classifying the agent within a group of agents having in common one or more mechanisms of action.

As described herein, the method of determining a mechanism of action of a combination of agents involves contacting a plurality of populations of cells with a combination of agents to be assessed wherein each population of cells has one gene of interest that is not functional (e.g., not expressed). In a particular aspect, the method of determining a mechanism of action of a combination of agents involves contacting a plurality of populations of cells with a combination of agents to be assessed wherein each population of cells have one gene of interest targeted by a small hairpin (shRNA). As is known in the art, shRNA is a ribonucleic acid (RNA) polymer that is designed based on the study of naturally-occurring hairpin RNAs involved in RNA interference (RNAi). shRNA function in the cell is to drive the degradation of messenger RNAs (mRNAs) in a sequence-specific manner. More specifically, shRNA is a short sequence of RNA which makes a tight hairpin turn and can be used to silence gene expression via RNA interference (e.g., Paddison, P., et al., Genes Dev. 16 (8): 948-958 (2002)). That is, in one aspect of the method described herein, each shRNA acts to knock down one gene.

In particular aspects, the method comprises introducing the plurality of shRNAs targeting the plurality of genes of interest into the plurality of populations of cells, wherein each shRNA targets one gene of interest that regulates cell death, wherein each population of cells have one gene of interest targeted. In other aspects, the method can comprise introducing the plurality of shRNAs which suppresses expression of the plurality of genes into the plurality of cells, wherein each shRNA suppresses expression of one gene that regulates cell death, and one gene is suppressed in each cell.

As will be appreciated by those of skill in the art there are a number of genes that regulate cell death. In a particular aspect, the gene that regulates cell death is a gene in the Bcl2 family of genes, a p53 gene, or a p53-activating kinase gene. Examples of a gene in the Bcl2 family of genes includes a Bax gene, Bak gene, a Bok gene, a Bim gene, a Bid gene, a Puma gene, a Noxa gene, a Bad gene, a Bmf gene, a Bik gene, a Hrk gene, a Bclx gene, a Bclb gene, a Bclw gene, an A1 gene, a Bclg gene, a Mil1 gene, a Mule gene, a BPR gene, a BNIP gene, a Bcld gene, a Bcl2 gene, or a Mcl 1 gene. Examples of a p53 activating kinase gene include an ATM gene, an ATR gene, a Chk1 gene, a Chk2 gene, a DNAPKcs gene, a Smg-1 gene, a JNK1 gene or a p38 gene.

In the methods of the invention a plurality of genes that regulate cell death are targeted in the plurality of cell populations. In particular aspects, three genes, four genes, five genes, six genes, seven genes, eight genes, nine genes, ten genes, eleven genes, twelve genes, thirteen genes, fourteen genes, fifteen genes, sixteen genes, seventeen genes, eighteen genes, nineteen genes, twenty genes, twenty one genes, twenty two genes, twenty three genes, twenty four genes, twenty five genes, twenty six genes, twenty seven genes, twenty eight genes, twenty nine genes, thirty genes or more are targeted by the corresponding shRNAs. As will be appreciated by those of skill in the art, libraries encompassing hundreds and thousands of such genes can be used in the methods described herein.

The particular genes chosen for targeting can thereby provide a particular shRNA signature of the combination of agents when assessed using the methods provided herein. For example, in a particular aspect, the plurality of genes targeted by the corresponding shRNAs are ATM, Chk2 and p53 genes, thereby allowing one to characterize the mechanism of action of a combination of agents as a shATM-Chk2-p53 'resistance signature'. In another aspect, the plurality of genes targeted by the corresponding shRNAs are p53, ATR, Chk1, Chk2, Smg-1, DNA-PKcs, Bok and Bim genes, thereby allowing one to characterize the mechanism of action of a combination of agents as a shp53, ATR, Chk1, Chk2, Smg-1, DNA-PKcs, Bok, Bim 'resistance signature'. As will be appreciated by those of skill in the art, other resistant signatures can be determined as described herein.

In the methods of the invention, the shRNAs can be introduced into the cells using a variety of methods. For example, as described herein a viral vector is used. Numerous viral vectors that can be used in the methods are known to those of skill in the art. Specific examples include a retroviral vector, an adenoviral vector and the like.

As will be appreciated by those of skill in the art, the vector can include other components. In a particular aspect, the viral vector further expresses a marker gene. Any variety of marker genes can be incorporated into the viral vector. In one aspect, the marker gene is a fluorescent marker gene. In a particular aspect, the marker gene is green fluorescent protein (GFP) gene.

Marker genes and the expression thereof can be measured in the cell populations using a variety of techniques known in the art. Thus, the methods described herein can further comprise measuring the marker gene (e.g., a fluorescent marker gene or GFP gene) expression level in each population of cells. In one aspect, flow cytometry is used to measure the marker gene or expression thereof.

As described herein a responsiveness of each population of cells to the combination of agents is determined, thereby obtaining the shRNA signature of the agent so as to identify one or more genes that mediate a response to the agent. Examples of a type of responsiveness that can be determined include resistance or sensitivity to the combination of agents. In one aspect, the responsiveness of each population of cells to the a combination of agents is a relative level of chemo-resistance and sensitization conferred by each shRNA. In a particular aspect, the responsiveness is a relative survival rate of each population of cells compared to control cells that do not contain said shRNA targeting the gene of interest.

The determination of responsiveness can be determined using a variety of methods. In one aspect, the determination of the responsiveness is accomplished using cell flow cytometry, hybridization techniques or sequencing techniques.

In the methods of the invention the plurality of populations of cells can be contacted with the combination of agents for any suitable amount of time. In some aspects, the plurality of populations of cells are contacted once with the combination of agents. In other aspects, the plurality of populations of cells are contacted repeatedly (more than once) with the combination of agents. In addition, the plurality of populations of cells can be contacted with the combination of agents for about 1 hour, 4 hours, 8 hours, 12 hours, 16 hours, 20 hours, 24 hours, 28 hours, 32 hours, 36 hours, 40 hours, 44 hours, 48 hours, 52 hours, 56 hours, 60 hours, 64 hours, 68 hours, 72 hours, 76 hours, 80 hours, 84 hours, 88 hours, 92 hours, 96 hours, 100 hours or longer.

In the methods described herein, the concentration (e.g., amount) of the combination of agents that is contacted with the plurality of populations of cells will vary and will depend on a variety of factors (e.g., the type of combination of agents being assessed; the type of response being sought, etc). For example, the concentration of the combination of agents that is contacted with the populations of cells can be based on the lethal dose (LD) of the combination of agents or one or more agents within the combination of agents, if known. The LD of the combination of agents that can be used in the methods includes the lethal dose that is sufficient to kill 50% of a cell population (LD50), 60% of a cell population (LD60), 70% of a cell population (LD70), 80% of a cell population (LD80), 90% of a cell population (LD90), or 100% of a cell population (LD100). In particular aspects, the agent is used in an effective amount to induce a response in cells that do not contain said shRNA targeting said gene of interest.

Any of a variety of cells can be used in the methods of the invention. In one aspect, the cells are mammalian cells. Examples of mammalian cells include primate cells (e.g., human cells), murine cells (e.g., mouse cells, rat cells), feline cells, canine cells, bovine cells and the like. In a particular aspect, the cells are from a pathological or diseased source. For example, the cells can be tumor cells. Examples of tumor cells include lymphoma cells, acute lymphocytic leukemia cells and the like.

As will be appreciated by those of skill in the art, the methods described herein can further comprise comparing the responsiveness of each population of cells to the combination of agents to a control. As will be apparent to those of skill in the art, a variety of suitable controls can be used. In one aspect, the control is a population of cells into which the shRNA targeting the gene of interest has not been introduced.

As will also be appreciated by those of skill in the art, the methods of the invention can be performed in vitro, as described herein. Alternatively, or additionally, the methods described herein can be performed in vivo. An example of an in vivo method involves the use of a pooled shRNA format. In this aspect, shRNAs are pooled and transduced into a target cell population and the population is then engrafted into a recipient non-human mammal such as a rodent (e.g., a mouse or a rat). A pretreatment baseline is established by sequencing or hybridization. The non-human mammals are dosed with the combination of agents and following treatment, reassessed for the shRNA pool composition.

As shown herein, the methods of the invention can also be automated. In one aspect, the methods can further comprise using an algorithm to cluster a plurality of agents into groups based on the responsiveness of each population of cells to each agent.

Figure 8:
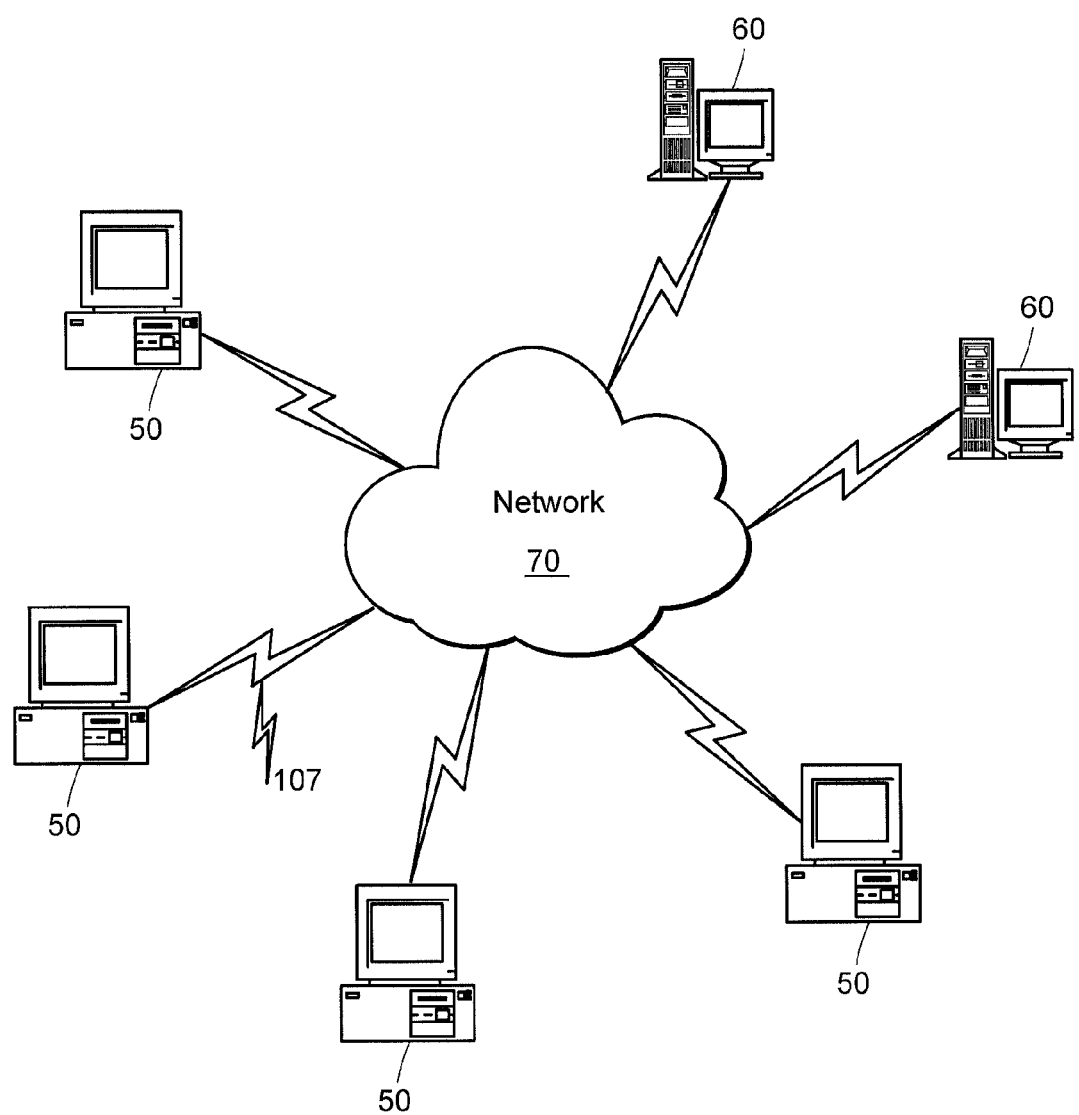
FIG. 8: Illustration of a computer network or similar digital processing environment in which the present invention may be implemented.

FIG. 8 illustrates a computer network or similar digital processing environment in which the present invention may be implemented. For example, a computer(s)/devices 50 and server computer(s) 60 provide processing, storage, and input/output devices executing application programs and the like. The computer(s)/devices 50 can also be linked through communications network 70 to other computing devices, including other client devices/processes 50 and server computer(s) 60. A communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 9:
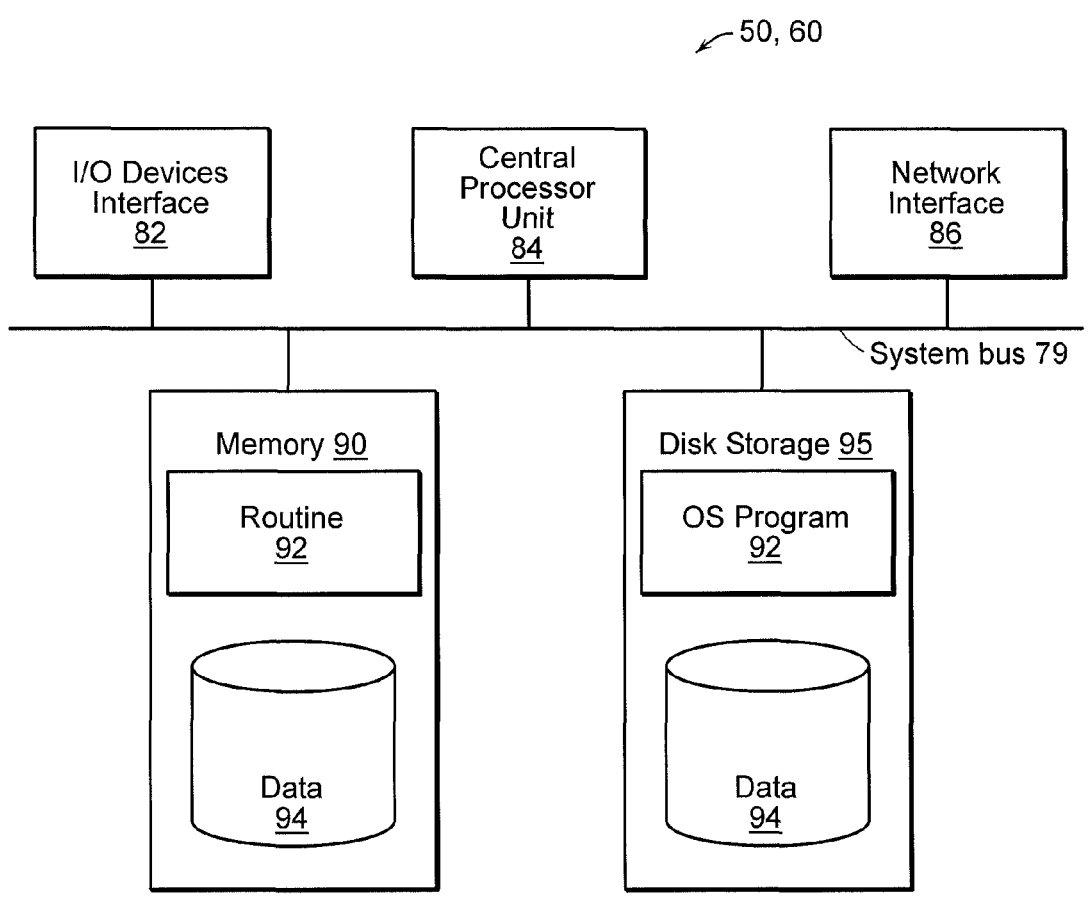
FIG. 9: Diagram of the internal structure of a computer (e.g., client processor/device 50 or server computers 60) in the computer system of FIG. 15.

FIG. 9 is a diagram of the internal structure of a computer (e.g., processor/device 50 or server computers 60) in the computer system of FIG. 8. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 8). Memory 90 provides volatile storage for computer software instructions 92 and data 94 used to implement an embodiment of the present invention. Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The method of characterizing a mechanism of action of a combination of agents described herein has other useful applications. For example, the methods described herein can be used to assess whether a drug that is currently being used to treat a patient or patient populations (e.g., a cancer patient or cancer patient populations) can be combined with one or more agents (e.g., drugs) to treat that patient or patient population. In addition, the methods described herein can be used to assess whether one or more drug formulations alter the mechanism of action of a drug or drugs.

Accordingly, in another aspect, the invention is directed to a method of determining whether a patient population treated with a first agent would benefit from a treatment using the first agent in combination with one or more additional agents. The method comprises contacting a plurality of populations of cells with a combination of agents to be assessed wherein the combination comprises the first agent and one or more additional agents, and wherein each population of cells have one gene of interest targeted by a small hairpin RNA (shRNA), said gene of interest regulates cell death and a plurality of genes that regulate cell death are targeted in the plurality of populations of cells. A responsiveness of each population of cells to the combination of agents is determined, thereby obtaining an shRNA signature of the agent so as to identify one or more genes that mediate a response to the combination of agents. The shRNA signature of the combination of agents is compared to the shRNA signature of the first agent, wherein if the shRNA signature of the combination of agents is the same, substantially the same or similar, to the shRNA signature of the first agent, then the patient population treated with the first agent would benefit from a treatment using the first agent in combination with the one or more additional agents.

In yet another aspect, the invention is directed to method of determining whether a formulation of one or more agents maintains a mechanism of action of the one or more agents when unformulated. The method comprises contacting a plurality of populations of cells with a formulation of the one or more agents to be assessed, wherein each population of cells have one gene of interest targeted by a small hairpin RNA (shRNA) and wherein said gene of interest regulates cell death and a plurality of genes that regulate cell death are targeted in the plurality of populations of cells. A responsiveness of each population of cells to the formulation of the one or more agents is determined, thereby obtaining an shRNA signature of the formulation of the one or more agents so as to identify one or more genes that mediate a response to the formulation of the one or more agents. The shRNA signature of the formulation of the one or more agents is compared to the shRNA signature of the one or more agents when unformulated wherein if the shRNA signature of the formulation of the one or more agents is similar to the shRNA signature of the one or more agents when unformulated, then the formulation maintains the mechanism of action of the one or more agents when unformulated.

Exemplification: Genetic Mechanisms of Combination Chemistry

Methods
Cell Culture

Eµ-Mycp19$^{Arf-/-}$ lymphoma cells and primary isolates from spontaneous Eµ-Myc primary tumor cells were cultured using established protocols (Burgess, D. J. et al. Proc Natl Acad Sci USA 105, 9053-9058 (2008)).
shRNA Signatures All shRNAs were expressed in the MLS retroviral vector39 and were previously validated for knockdown and single agent phenotypes and off target effects34. Informatics is performed as in Jiang, H., et al., Nature Chemical Biology 7, 92-100 (2011) which is incorporated herein by reference.
Combination Dosings All combination dosings are performed at LD80-90s and single drug contributions are dosed at equivalently single drug killing (to within 10% single drug cell death). Principal Components analysis was performed with the princomp.m function.
Primary Lymphomas C57/BL6 Eµ-Myc transgenic mice were obtained from Jackson Labs (Bar Harbor, Me.) and were monitored for the spontaneous development of lymphoid tumors. Three doses of single drugs that encompassed the LD50 for the control Eµ-Mycp19arf-/- were used to dose the primary lines. The relative PI-negative percentages were averaged across all cell lines. The across cell line averages were used to dose the four drug combination. The LD50-60 for each single drug dose across all of the cell lines was combined to form the CVAD dosing.

Partial Genome Scale Screen

The large scale 10 k library was a gift of Johannes Zuber and Scott Lowe, the 8 shRNA signature was spiked in at 1:10000. Library infected cells were dosed with single and CVAD/CHOP combinations at an LD70-80 to preserve representation and prevent bottlenecks. Hairpin representation was assessed using a barcoded half-hairpin solexa sequencing approach. For more information see the supplementary methods.

shRNAs

All shRNAs were expressed in the MLS retroviral vector (Dickins, R. A. et al. Nat Genet 37, 1289-1295 (2005)) and were previously validated for knockdown and single agent phenotypes (Jiang, H., et al., Nature Chemical Biology 7, 92-100 (2011)). shRNA plasmids were packaged in phoenix cells, and viral supernatants were concentrated using co-polymer precipitation method. $5 \times 10^4$ initial cells were infected to between 10 and 20% of the total population. All signatures include replicates from at least two distinct infections. Combination vector control dosings were performed to rule out combination specific effects of the vector alone.

Pairwise Drug Interactions

Cytotoxic agents from distinct functional categories34 were dosed in a pairwise fashion. Dosing was done in two dimensional dose response matrices. At least one compound from each category was tested against all other functional categories. Cell death was normalized to 100% and the relative PI negative measurement was reported. Every point in the dosing matrix that contained a combination of drugs was used to estimate Bliss Independence at that point. A Mann-Whitney U-test was used to compare the pairwise drug interactions for combinations that came from a CHOP/CVAD functional category (Dox-CBL, Dox-Vin, CBL-Vin, Dox-Taxol, Etoposide-Taxol, Dox-Mitomycin C (MMC), Tax-MMC) with the remainder of the dataset.

Combination Dosings

All drug dosings were normalized by LD numbers, and were monitored after every independent dosing to ensure accuracy and reproducibility. Combination dosings for shRNA signature measurements were performed in a dose response matrix form. The matrix was assessed for the % PI negative population at 48 hours after treatment. Signatures were measured at 72 hours after treatment. The matrix position for the combination signature measurements was determined in the same manner as in FIG. 2b. Drug doses producing similar levels of toxicity (within 10% PI negative of each other), and combining to produce an LD80-90, were used. PI negative values were plotted relative to shRNA-GFP hairpin enrichment values and significant ($r2>0.6$) dose-response trends are accounted for with a linear model and normalized to an LD85 to eliminate dosing as a variable.

Primary Tumor Dosings

C57/BL6 Eµ-Myc transgenic mice were obtained from Jackson Labs (Bar Harbor, Me.) were monitored for the spontaneous development of lymphoid tumors. Upon the onset of morbidity, mice were euthanized according to established MIT veterinary protocols. Tumors were harvested disassociated, and grown in culture. The fraction of primary tumors that were capable of growing in tissue culture was used to assess drug response. Three doses of single drugs that encompassed the LD50 for the control Eµ-Myc;p19$^{Arf-/-}$ were used to dose the primary lines. The relative PI-negative percentages were averaged across all cell lines. The across cell line averages were used to dose the four drug combination. The LD50-60 for each single drug dose across all of the cell lines was combined to form the CVAD dosing.

Combination probKNN Analysis

The Taxol/17AAG reference set included all reference set drug categories from the pairwise synergy screen. The Taxol/CBL prediction was obtained by grouping topoisomerase II poisons, crosslinking agents, and single strand break inducing agents together into one DNA damage category. The Dox-CBL prediction included the entire reference set as well.

Combination PCA Analysis

Rows of the PCA input were individual drug experiments and the 8 columns correspond to the 8-shRNA signature genes. PCA was performed using the Matlab princomp.m function. Scores plots indicate the projection of drug observations onto the latent variable projections. All matrices used as the input for PCA contained only the observations that were plotted.

Cell Line PCA Analysis

Figure 3A:
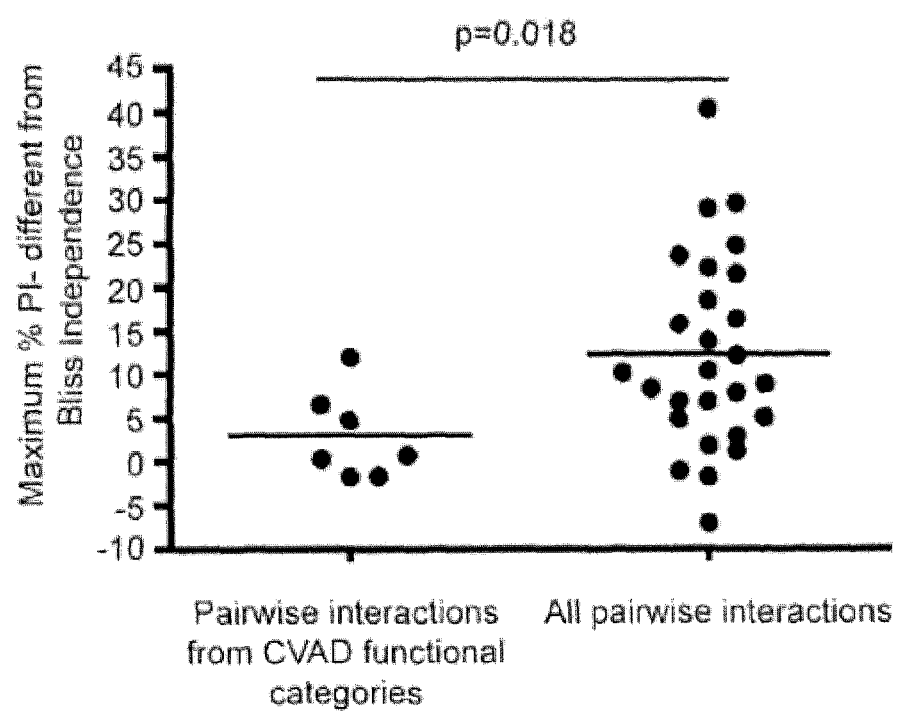
FIGS. 3a-3f: CHOP/CVAD components work via an averaging mechanism. (3a) A scatter plot compares bliss independence values for the pairwise combinations of cytotoxic CVAD/CHOP components to the rest of the dataset. Significance was determined using a Mann-Whitney Utest. (3b) Top: A PCA scores plot generated using alkylating agents, topoisomerase II poisons, and four independent Dox-CBL replicates. Bottom: Average single drug mechanisms and the combination Dox-CBL drug shRNA signature are shown. (3c) Top: A PCA scores plot for a PCA performed on all four component drugs and the combinations of (CA, CVA, and CVAD). The dexamethasone signature is taken at an LD70. The average trajectories of the combinations are indicated with vectors. Bottom: A heatmap of the 8shRNA signatures contained in the PCA. (3d) A schematic showing the generation of distinct lymphomas in mice. (3e) Top: A heatmap of the relative (to untreated) PI negative (%) values in distinct primary cell lines following treatment with increasing levels of single drugs. Bottom: A PCA loadings plot for the PCA performed on the above data. The variance explained by the first two principal components is indicated below the plot. (3f) Top: A heatmap of the relative (to untreated) PI negative (%) values in distinct primary cell lines that results from increasing levels of combination (CVAD) dosings. To create the combination, the average LD50-60 of each of the individual drugs across all primary cell lines was combined and then the combination was serially diluted. Bottom: a PCA loadings plot for the PCA performed on the above data. The variance explained by the first two principal components is indicated below the plot. The significance of the variance explained is compared to permuted matrices to assess statistical significance.
Figure 3B:
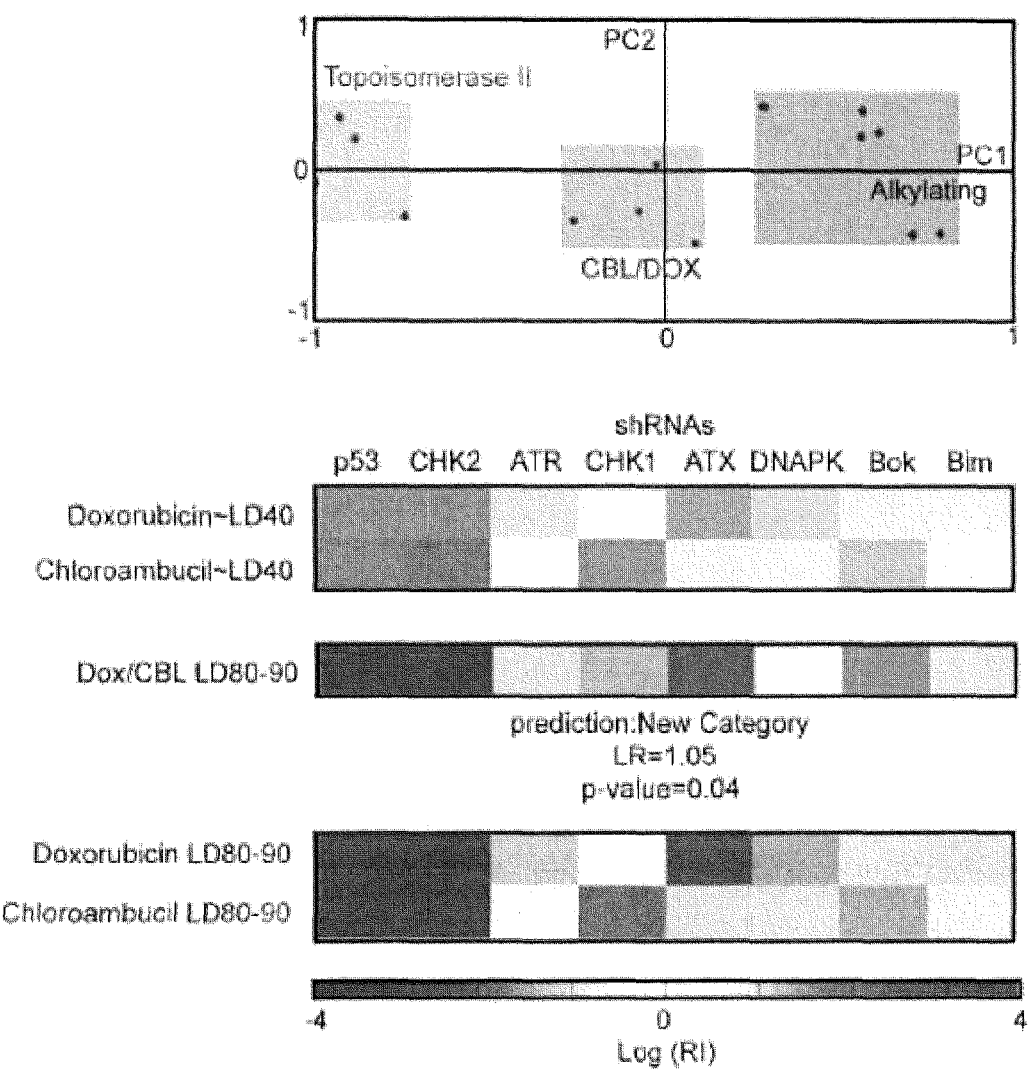
Figure 3C:
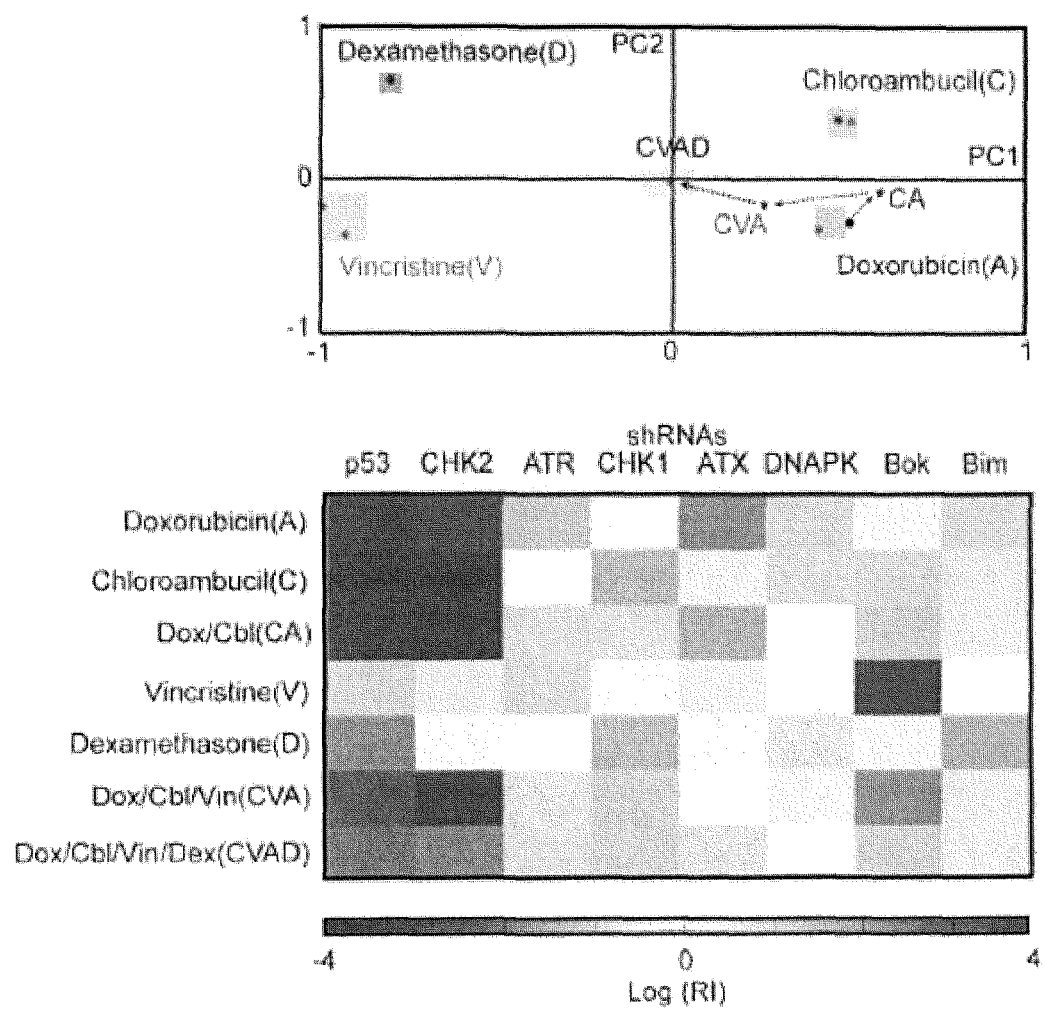
Figure 3D:
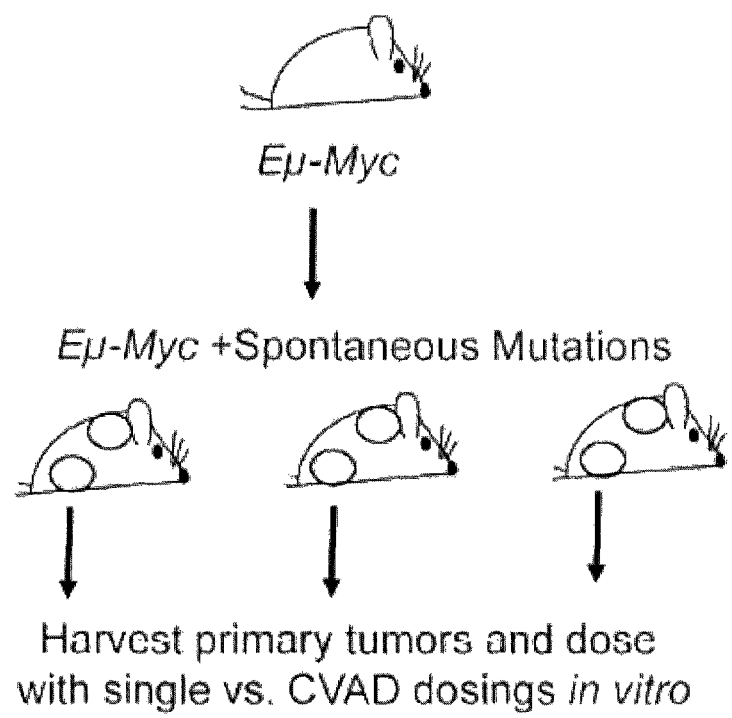
Figures 3E, 3F:
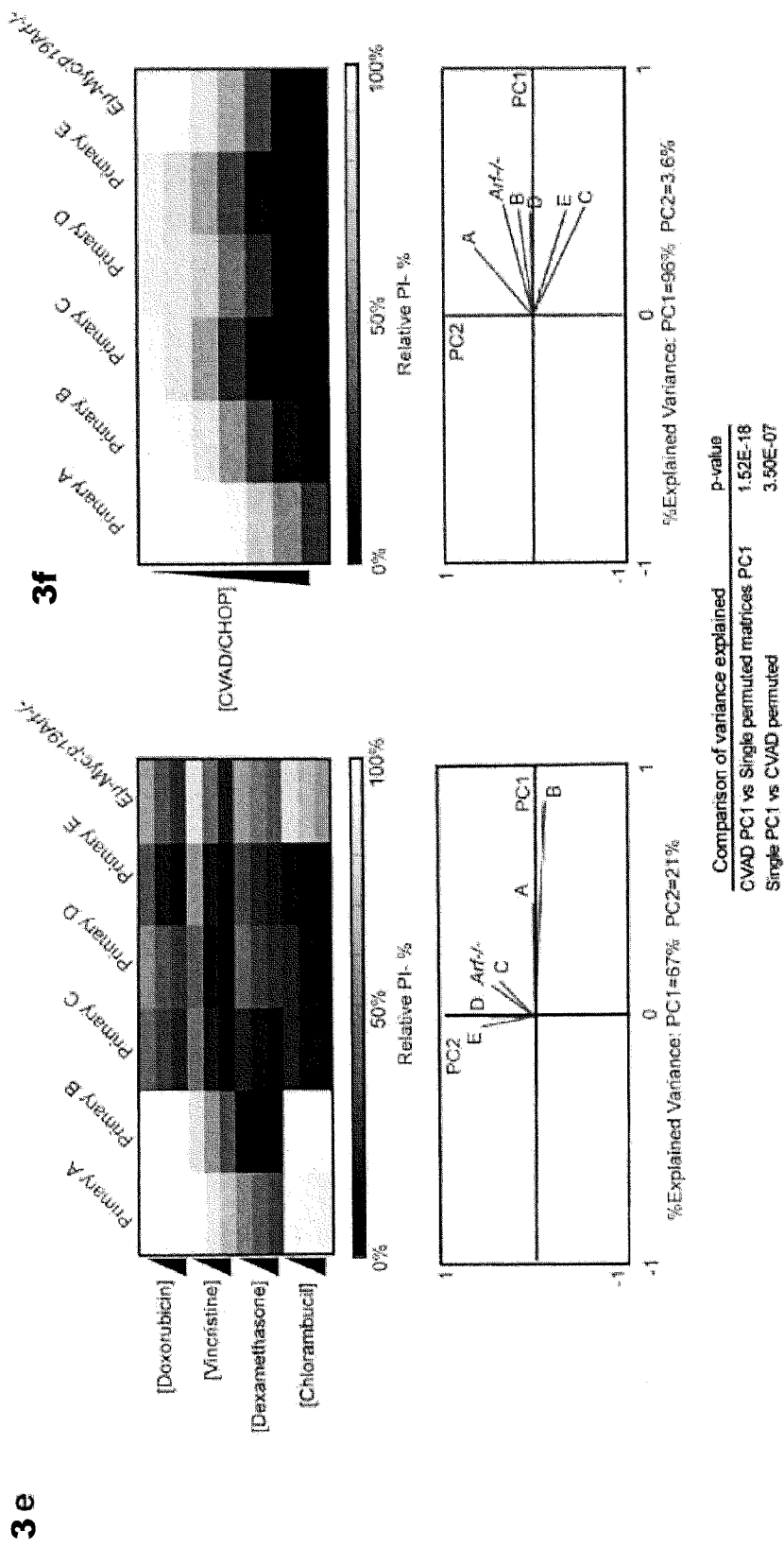

Matrices were organized as shown in FIGS. 3e and f. Different drugs and drug dosings constituted experimental observations. Different cell lines were treated as variables. As such, the loadings plots show the contribution of each cell line "variable" to the meta-variable or principal component. The percent of the variance explained by the model is calculated by totaling the latent vector and dividing each PC's value by the sum of the vector components. This tells how much of the total model fit is from each component. The significance of the percent of the variance explained by the principle components was determined by comparing the experimental results to 1,000 randomized matrices. These matrices were assembled by randomly drawing values for each column from the corresponding column of the experimental data, effectively reshuffling the rows of data within each column. PCA was executed on the 1000 randomized matrices and the percent of data explained by each principle component was determined. The mean and standard deviation of the percent of data explained by the 1st or the 2nd principle components for the 1,000 matrices was then used to execute z-tests.

10 k-Pooled Screen

Dosings: The second-generation shRNAmir30 partial genome-scale library (pool1) was obtained courtesy of Scott Lowe and Johannes Zuber. The 8-shRNA set was added to the library at 1:10000. Phoenix cells were used to package a mixed pool of retrovirus containing the 10 k library. 3 million 4-Myc;p19Arf-/- were infected to 50% GFP+ (MOI=1) and expanded in vitro for 2 days. Cells were then treated with an LD70-80 of single and combination drugs. A slightly lower drug dose was used to preserve pool representation. Cells were diluted 1:2 at 24 hours, % PI negativity was assessed at 48 hours and dosings with the desired amount of cell killing were resuspended in fresh media. Cells were allowed 2-3 days to recover to 80-90% viability, and frozen down for analysis.

Sequencing

Half hairpin barcodes were PCR amplified from genomic DNA. Distinct mutations in the 5' primer were used to barcode distinct drug treatments. The PCR products were then processed using the solexa genomic DNA preparation kit. Gel purified solexa input product was submitted to the Koch Institute genome analyzer.

Data Analysis

Raw read numbers (for exact matches only) between lanes were normalized by the number of total reads per lane. Raw read numbers for all barcodes in a lane were normalized across all lanes. These normalized reads were then filtered for further analysis. A threshold of >700 reads per hairpin in all three lanes sequenced was used to filter out low abundance reads. This yielded 6819 shRNAs. Of these 6819 shRNAs, 7 shRNAs from our 8-shRNA signature were represented. Hierarchical clustering on this data set was done using a correlation based metric and complete linkage. Averages, standard deviations and coefficients of variation were calculated. An absolute value of the Log 2(Treated reads/Control reads) greater than 2.5 (the CVAD shp53 value) for any drug/combination treatment was used as a filter for hairpins with high potency. This set was again filtered for reproducibility. A CV of 0.8 (a conservative estimate of 8-shRNA signature variability at high levels of enrichment or depletion) was used. This yielded a reproducible set of 93 hairpins for further analysis. In order to assess whether or not these 93 hairpins followed an averaging model, we used the 7 abundant shRNAs from the 8-shRNA signature as a set of positive controls. These 7 shRNAs are known to show an averaging effect in a GFP competition based experiment, so we used them to threshold our 93 shRNAs. shRNAs had to be two standard deviations different from the average deviation of the 8-shRNA signature set to be considered distinct from the averaging model. Example code for use in quantifying what percentage of a combination of drugs is coming from each drug in the combination

```
function [x,y]=Druglincomb(Dosemat)
% This function takes two dose responses and calculates
    each combination
% in the matx as a linear combination on the input singlets
    entryi,j=1 is
% the control
[m,n]=size(Dosemat);
% Normalize to the control
nmat=zeros(3,3)
xmat=zeros(3,3)
ymat=zeros(3,3)
Dosematnorm=Dosemat./Dosemat(1,1);
i=2;
while i<m+1
j=2;
while j<n+1
nmat(i-1,j-1)=Dosematnorm(1,j)./Dosematnorm(i,1);
ymat(i-1,j-1)=((-1/(1+nmat(i-1,j-1))))+1;
xmat(i-1,j-1)=1-ymat(i-1,j-1)
j=j+1;
end
i=i+1;
end
x=xmat
y=ymat;
end
```

Results

A commonly argued principal of combination therapy is that by combining agents with independent dose limiting toxicities, the cumulative dose of drugs can be greatly enhanced. While this is certainly a critical aspect of combinatorial efficacy (DeVita, V. T. & Schein, P. S. NEJM 288, 998-1006 (1973); Frei, E., 3rd. Cancer research 45, 6523-6537 (1985); Frei, E., 3rd, et al., Clinical Cancer Research 4, 2027-2037 (1998); Budman, D. R. et al. Journal of the National Cancer Institute 90, 1205-1211 (1998); Skipper, H. E., et al., Cancer Chemotherapy Reports. Part 1 35, 1-111 (1964)), it is difficult to separate dose effects from other variables in clinical trials. This lack of mechanistic resolution has limited the direct experimental interrogation of a variety of additional provocative hypotheses (Hucl, T., et al., Cell Cycle 6, 1336-1341 (2007)). In contrast with combination therapy, numerous biochemical and genetic approaches have been developed to examine the mechanisms by which individual small molecules exert their effects. Some of the most effective, and generalizable, methods have been based on phenotypic/molecular signatures of drug action (Hughes, T. R. et al. Cell 102, 109-126 (2000); Parsons, A. B. et al. Cell 126, 611-625 (2006); Ho, C. H. et al. Nature Biotechnology 27, 369-377 (2009); Rihel, J. et al. Science 327, 348-351 (2010); Perlman, Z. E. et al. Science 306, 1194-1198, (2004); Krutzik, P. O., et al., Nature Chemical Biology 4, 132-142, (2008)). Signatures are an attractive methodology to characterize combination mechanisms due to their validated resolution across drug categories of interest, and their relative position in cellular response networks (i.e., downstream of typical drug targets). In several landmark studies using *S. cerevesiae*, gene expression compendia ((Hughes, T. R. et al. Cell 102, 109-126 (2000), and later barcoded loss of function/ORF libraries (Parsons, A. B. et al. Cell 126, 611-625 (2006); Ho, C. H. et al. Nature Biotechnology 27, 369-377 (2009)) were used to effectively characterize individual small molecule mechanisms of action. Similar work done utilizing the NCI-60 cell lines (Weinstein, J. N. et al. Science 275, 343-349 (1997)) showed that signatures of inhibitory concentrations of cytotoxic drugs across diverse cancer cell lines can provide enough resolution to predict a novel small molecule's mechanism of action. Finally, mammalian transcriptional data has also been used to determine the mechanisms of small molecule action (Lamb, J. et al. Science 313, 1929-1935 (2006); Hieronymus, H. et al. Cancer Cell 10, 321-330 (2006)). However, despite the disseminated use of signatures for drug mechanism studies in diverse systems, none have examined mechanistic signatures of combination drugs.

Recently, it has been demonstrated that an 8 shRNA signature (shp53, shChk2, shChk1, shATR, shATX, shDNAPKcs, shBok and shBim) provides high quantitative resolution across diverse drug categories that include most established cytotoxic agents, as well as newer agents like HSP90 inhibitors, HDAC inhibitors, and categories of kinase inhibitors. This signature-based approach to the prediction of drug mechanisms of action compares the signature of a test compound to a reference set of single drug signatures possessing known mechanisms of action. Shown herein is that a signature-based platform with validated resolution over a breadth of drug categories shows similar resolution in the context of multi-drug combinations.

Figure 1B:
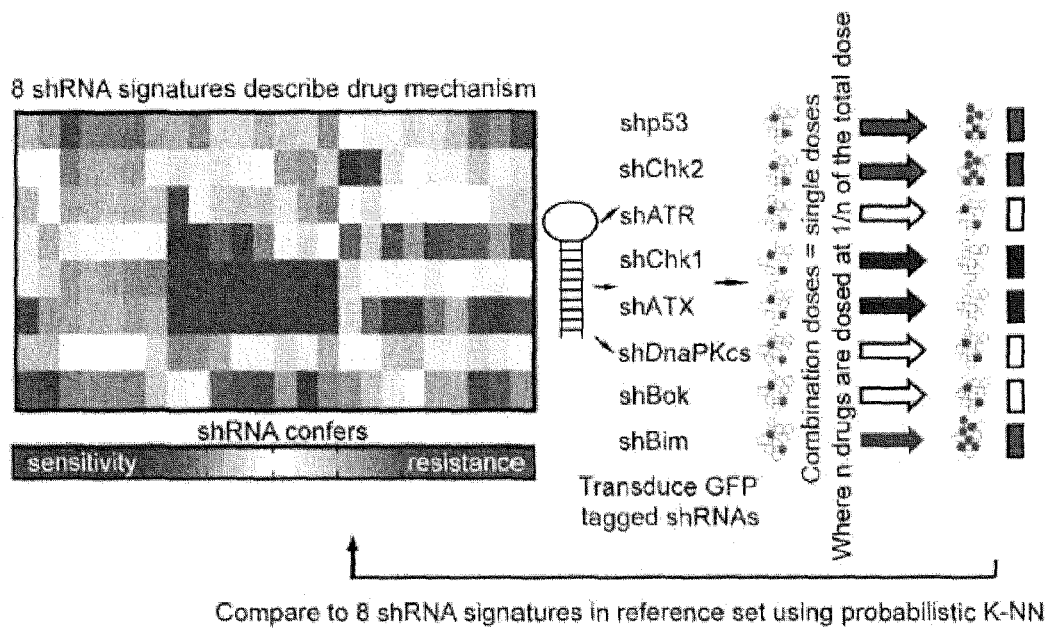
Figure 1C:
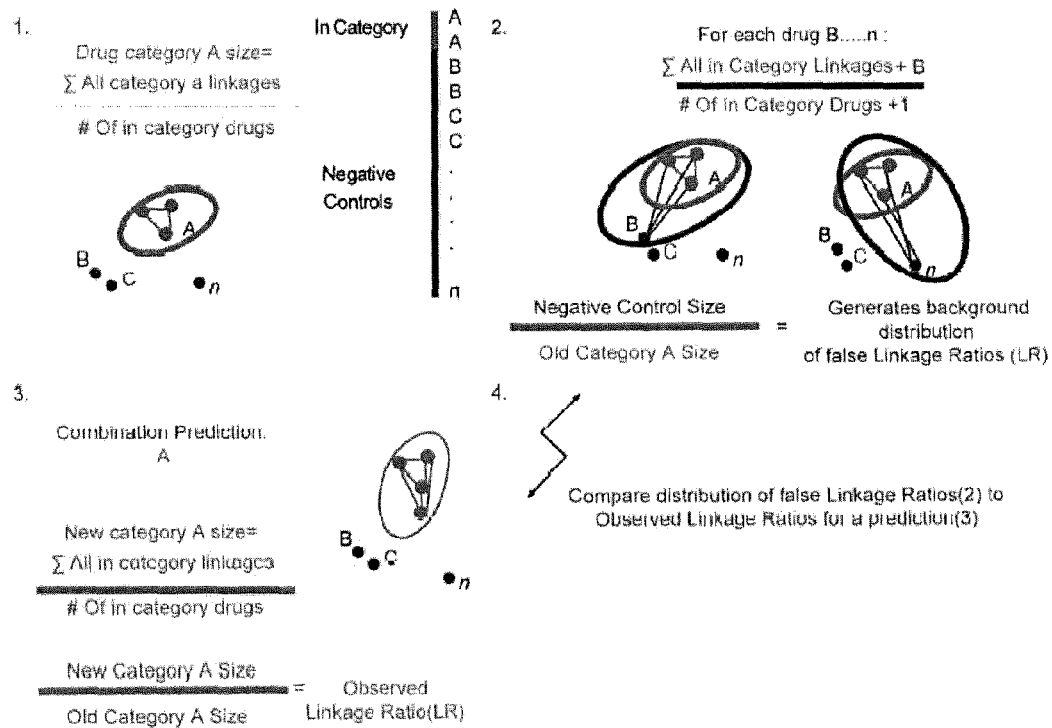
Figure 1D:
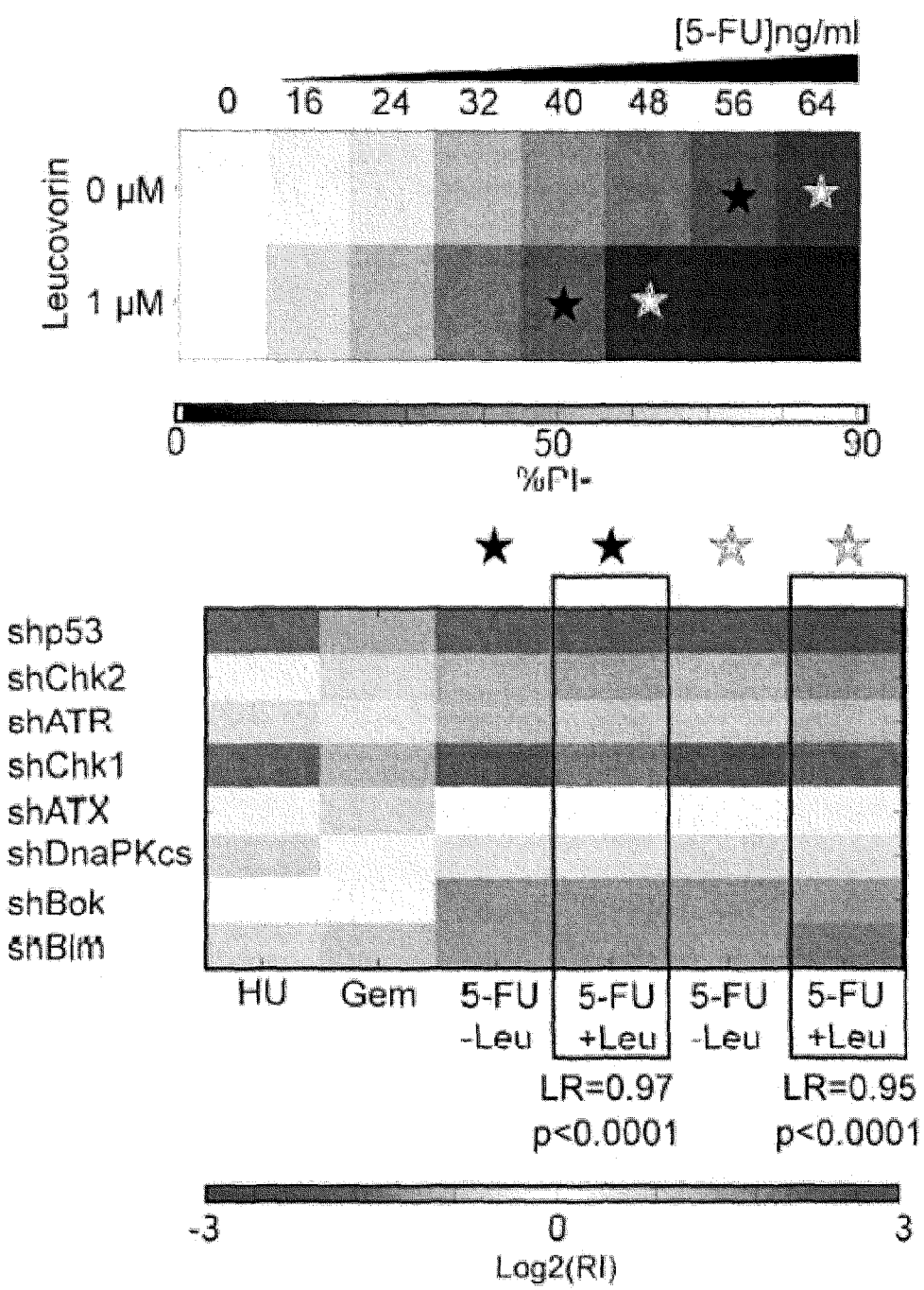

Combination therapies might be hypothesized to interact in two general ways: [a] one agent may simply reinforce the action of another agent; or [b] the two drugs may combine to exert effects that are distinct from either individual compound. Correspondingly, the combination drug shRNA signature would either [a] resemble that of one individual drug, or [b] exhibit distinct genetic dependencies. With respect to the latter possibility, a combination signature could be distinct from that of the individual component drugs in one of at least three ways: [i] it could average, or "homogenize", individual drug signatures; [ii] it could mimic a compound not present in the combination; or [iii] it could adopt an entirely novel signature (FIG. 1a). To extend the functional genetic signature-based framework to combination drug dosings, shRNA signatures of resistance or sensitivity in response to combinations of drugs that were controlled for dose level effects were created. All signatures in the single drug reference set were obtained at concentrations of drug that induce 80-90% cell death (LD80-90) in Eμ-Myc;p19$^{Arf-/-}$ lymphoma cells, a well characterized model of human Burkitt's lymphoma (Adams, J. M. et al. Nature 318, 533-538 (1985)). To allow for reference set comparisons, combination dosings at 80-90% cell death were achieved by dosing single drugs at equivalent levels of single agent killing such that each drug contributed equally to the total cell death (FIG. 1b). These combinations were then quantitatively compared using probabilistic nearest neighbors analysis (FIG. 1c).

While combination therapies are the standard of care for nearly all disseminated human cancers, only the interaction of 5-fluorouracil (5-FU) and leucovorin has a well-characterized combination mechanism of action. Leucovorin exerts a synergistic effect indirectly, by enhancing the inhibition of thymidylate synthase by the nucleoside analog 5-FU (Longley, D. B., et al., Nature Reviews. Cancer 3, 330-338 (2003)); this inhibition depletes cellular nucleotide levels and induces cytotoxicity. Thus, it was reasoned that this drug combination could be used as a proof of principal. Specifically, a signature of leucovorin plus 5-FU should resemble the single drug 5-FU signature but at a lower 5-FU concentration. It was observed that dosing lymphoma cells with leucovorin elicited no cell death at 1 μM but the addition of 1 μM leucovorin potentiated 5-FU action (FIG. 1 d). Moreover, the 8 shRNA signature for 5-FU plus leucovorin closely resembled 5-FU and was significantly ($p<0.0001$) predicted by probabilistic nearest neighbors analysis to be a nucleotide depletion agent. This indicated that the known biochemical mechanism of 5-FU and leucovorin is the relevant mechanism of cell death induction in Myc;p19$^{Arf-/-}$ lymphoma cells, and indicates that the signature-based approach offers resolution for combination drug mechanisms.

Figure 2A:
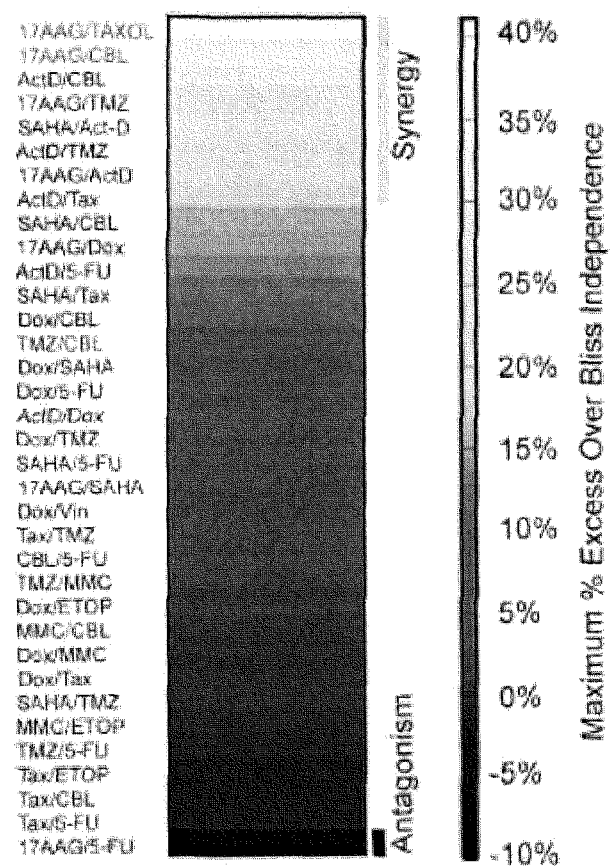
FIGS. 2a-2d: A pairwise drug interaction screen identifies highly synergistic combinations whose mechanism resembles single drug action. (2a) A pairwise drug screen performed on the indicated drugs is quantified by maximum % excess PI over a control additive model and rank ordered. Synergy and antagonism are indicated. (2b) Response surface diagrams of 17AAG in combination with Taxol and CBL. Surface color corresponds to the level of synergy. Colored stars indicate equivalent single drug dosings that combine to produce LD80-90 of the combination doses (demarcated by black stars). (2c) Signatures of 17AAG, Taxol, and CBL action at low single drug doses that combine to produce synergistic LD80-90 signatures, compared with single drug LD 80-90s. (2d) PCA "scores" plots of single and combination drug action allow for the visualization of the 8 shRNA signature predictions.
Figure 2B:
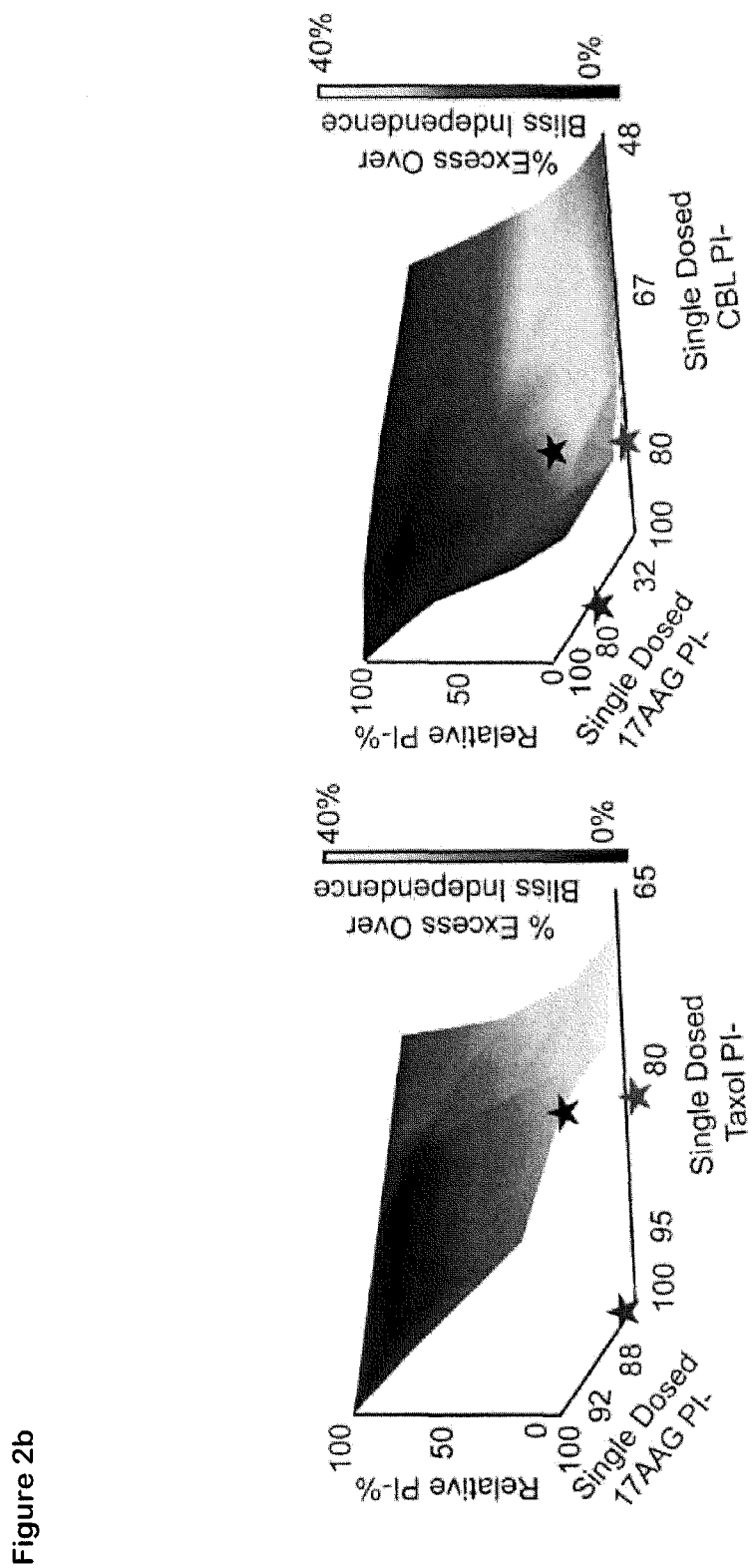
Figure 2C:
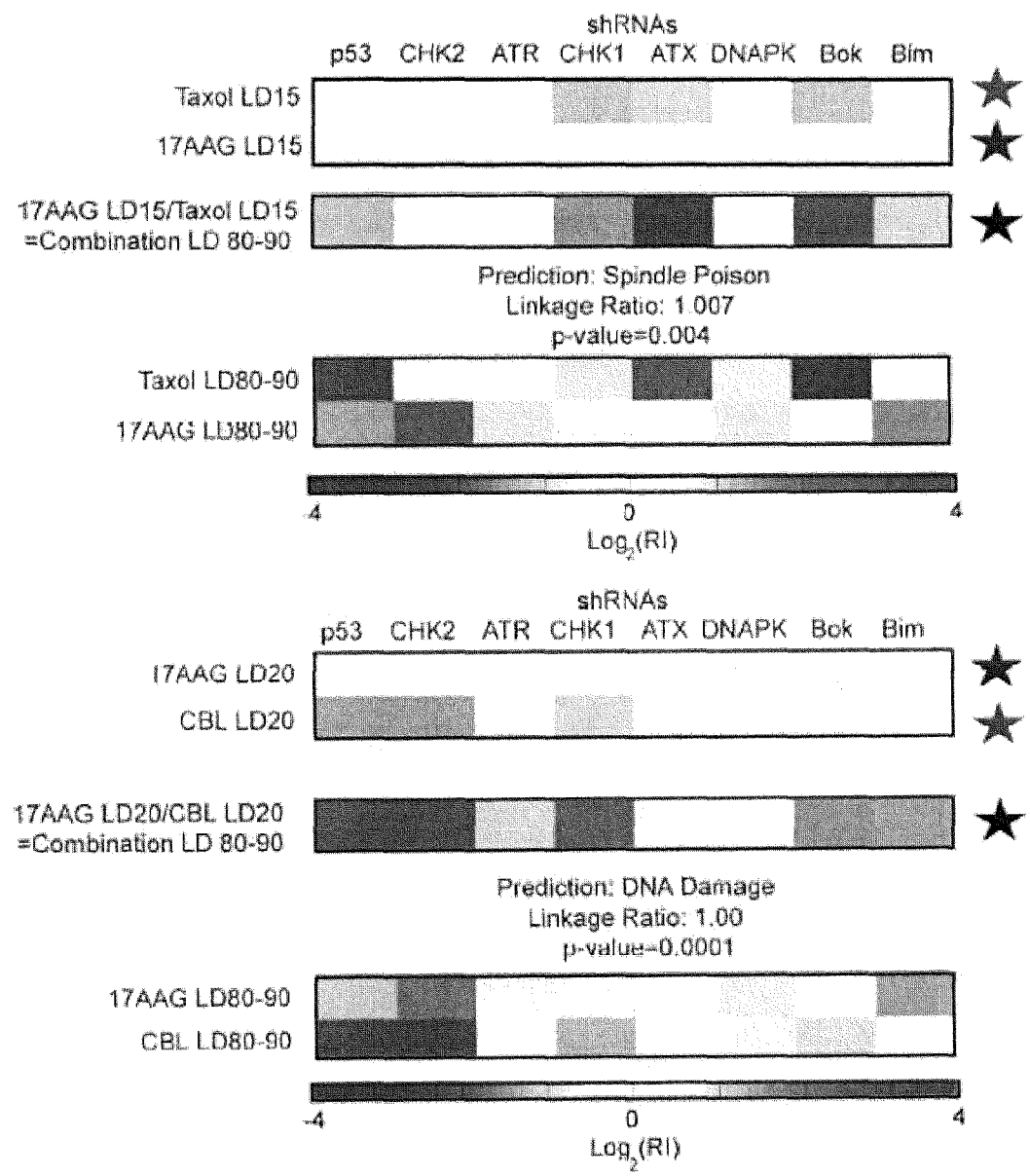

In order to take a non-biased approach to study combination drug mechanisms, all pairwise interactions between distinct functional categories of cytotoxic agents upon which the 8-shRNA signature has established resolution were examined (FIG. 2a). Initially, the two most synergistic combinations from our pairwise interaction screen were examined: 17AAG (an Hsp90 inhibitor) combined with Taxol (a spindle poison), and 17AAG combined with Chlorambucil (abbreviated CBL, a DNA alkylating agent) (FIGS. 2a and 2b). Specifically, concentrations of single drugs that individually induced single drug cell death in ~15% (for both 17AAG and Taxol) and ~20% (for both 17AAG and CBL) of the population were sufficient to elicit a combination LD of 80-90% (FIG. 2b). Consistent with this high level of synergy, control signatures taken at the respective single drug LD15s or LD20s exhibited little to no shRNA-mediated resistance or sensitivity (FIG. 2c). However, upon combination, the LD80-90s of 17AAG-Taxol and 17AAG-CBL elicited robust phenotypic signatures. Comparison of 17AAG-Taxol's signature to our single drug reference set indicated that this combination exhibited a spindle poison-like mechanism of action ($p=0.004$) (FIG. 2c). This evidence favored a model whereby 17AAG acts to strengthen taxol-induced cytotoxicity. Similarly, the signature for the 17AAG and CBL combination matched a DNA damage-like mechanism of action ($p=0.0001$), indicating that 17AAG synergized with CBL by promoting CBL's genotoxic activity (FIG. 2c).

Figure 2D:
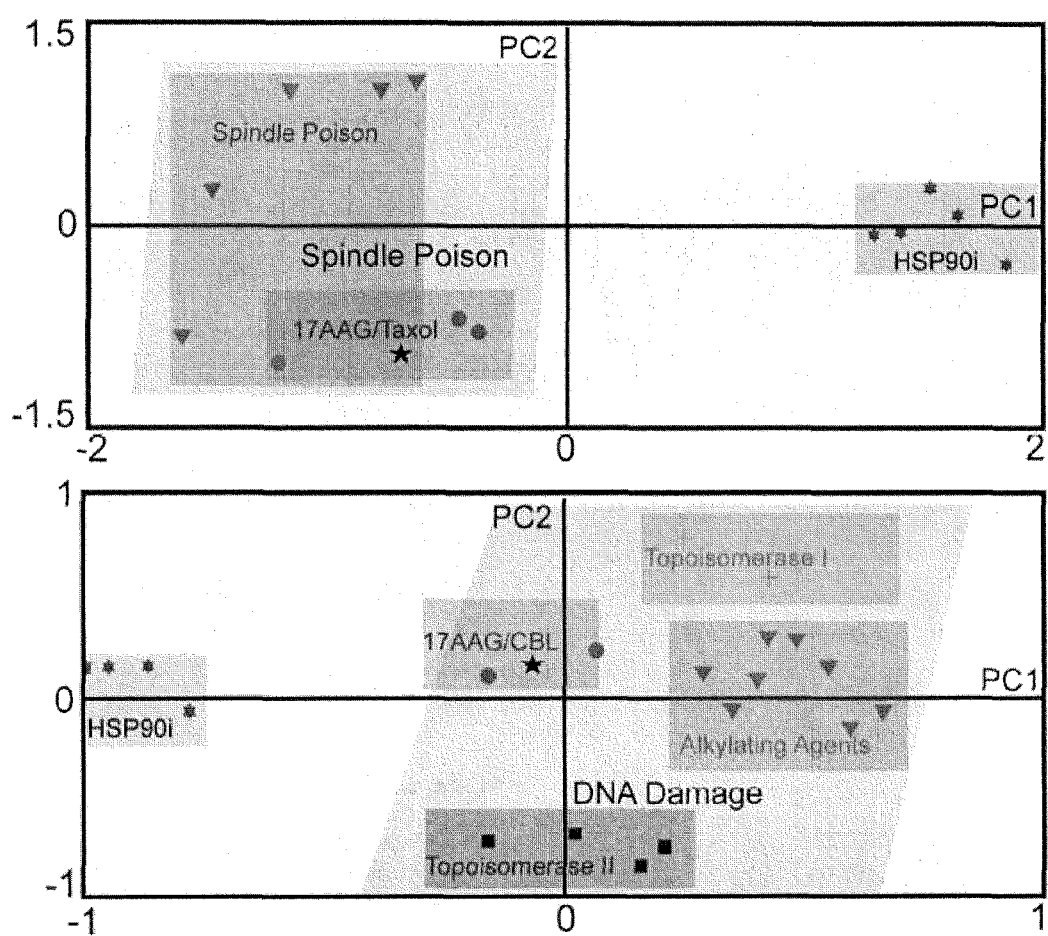

To examine these mechanistic predictions, Principal Components Analysis (PCA) was performed. In PCA, large dimensional datasets with many variables (here 8 variables, 1 for each shRNA in the signature) are collapsed onto composite variables, termed principal components, which represent a weighted combination of the 8 original primary variables. Consequently, observations of single drugs and drug combination behaviors can be replotted in 1, 2, or 3 dimensions to facilitate visual analysis and further interpretation of the statistical predictions. Replotting of Hsp90 inhibitors and spindle poisons alongside the 17AAG-Taxol combination revealed a clear separation of Hsp90 inhibitors from spindle poisons along a single composite variable: principal component 1 (PC1) (FIG. 2d, top). Furthermore, 17AAG-Taxol clearly mapped adjacent to the spindle poisons, supporting the prediction that 17AAG reinforces a taxol-like mechanism of action. A similar separation along the first principal component was seen with Hsp90 inhibitors in relation to DNA damaging agents (FIG. 2d, bottom). Plotting 17AAG-CBL, the closer proximity of the 17AAG-CBL to other DNA damaging agents indicates a genotoxic mechanism for this combination. Taken together, these data indicated that highly synergistic combinations act by potentiating an individual drug's mechanism of action.

Surprisingly, while drug synergy might be expected to translate into combination efficacy, the 17AAG-Tax and 17AAG-CBL drug combinations are not currently in clinical use—despite the inclusion of 17AAG-Tax in clinical trials (Ramalingam, S. S. et al. Clinical Cancer Research 14, 3456-3461 (2008)). Thus, combination regimens that are now the standard of care for B cell malignancies were examined. Given that the Myc;p19$^{Arf-/-}$ lymphoma cells are a well-established mouse model of Burkitt's lymphoma (a high grade Non-Hodgkin's lymphoma), combinations of commonly used therapeutics that comprise drug regimens for Non-Hodgkin's lymphoma (referred to as CHOP) or, more specifically, for Burkitt's lymphoma (referred to as CVAD) were reexamined. The induction arm of both regimens utilizes cyclophosphamide, Vincristine (Vin), doxorubicin (Dox), and a glucocorticoid receptor agonist (dexamethasone or prednisone). However, since cyclophosphamide requires activation in vivo, another nitrogen mustard, CBL, which has shown similar in vivo efficacy in clinical trials of lymphoma chemotherapy, was utilized (Carbone, P. P. et al. Cancer Research 28, 811-822 (1968)). Surprisingly, in the pairwise synergy screen, drugs from the cytotoxic functional categories of CHOP/CVAD exhibited significantly less pairwise in vitro synergy than the rest of the dataset ($p=0.018$) (FIG. 3a). Thus CHOP/CVAD efficacy cannot be attributed to component drug synergy.

To investigate CHOP/CVAD components, Dox and CBL were combined to obtain a combination LD80-90. Notably, unlike the synergistic drug combinations examined previously, the shRNA signature for this drug combination indicated a mechanism of action distinct from both component drugs (FIG. 3b). PCA visualization clearly separated topoisomerase II poisons like Dox from DNA alkylating-like agents along PC1 (FIG. 3b). Furthermore, the Dox-CBL combination dosings clustered around the origin of the PCA plot, indicating a relative averaging of the individual drug signatures—i.e., the remarkable elimination of contrasting shRNA-conferred behaviors exhibited for the individual drugs. For example, the diminution of DNAPKcs levels yielded sensitivity to Dox and resistance to CBL, but had no consequence in the face of a combination drug dosing. Thus, drug combinations can average single drug genetic dependencies, even to the point of essential neutrality.

Figure 5A:
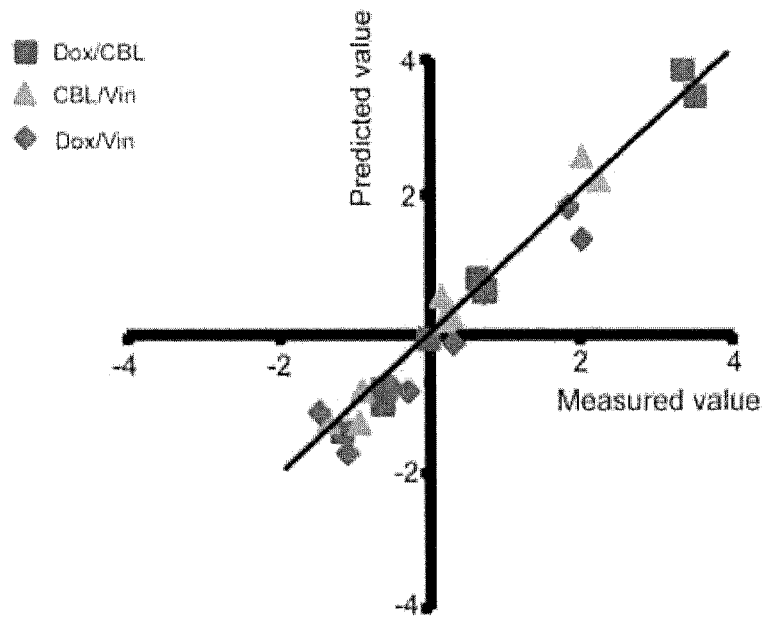
FIGS. 5a-5b: Examining the fit of CVAD components to an averaging model. (5a) Measured 8 shRNA signatures for CVAD/CHOP combinations: chlorambucil/vincristine (CBL/Vin), doxorubicin/vincristine (Dox/Vin) and doxorubicin/chlorambucil (Dox/CBL) from FIG. 3b for comparison, are plotted versus a 50%-50% average of their single drug signature. Points are color coded by dosings and the 45 degree line corresponds to a perfect averaging prediction. (5b) A comparison of the model fit. The goodness of fit to an average model is measured by squaring the deviation from the model and normalizing by the magnitude of the measurement. The average of this calculation is plotted on the Y axis. This measure is compared for the cytotoxic pairwise CVAD combinations, CVAD itself, and as a control, the synergistic 17AAG combinations that do not follow an averaging model.
Figure 5B:
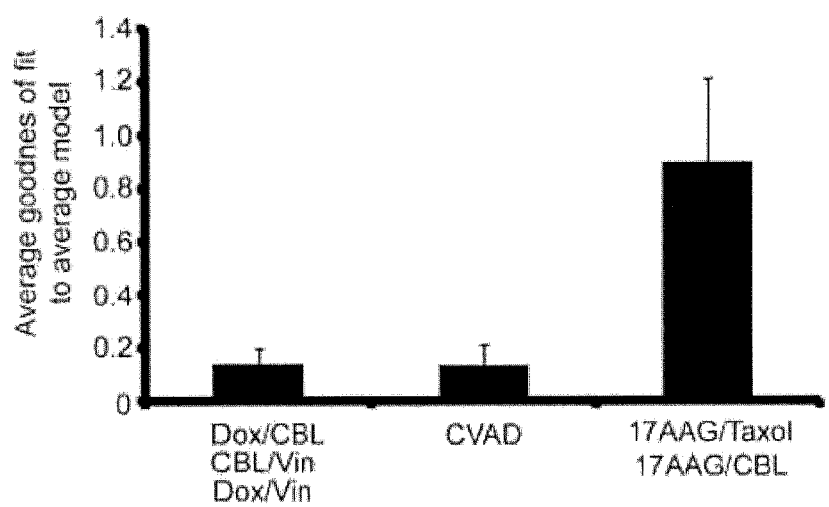

To test whether this averaging effect extended to the other cytotoxic components of CVAD/CHOP, signatures of CBL-Vin and Dox-Vin were examined and compared to what would be predicted by taking the mean of their single drug effects (FIG. 5a). It was found that these other combinations of CVAD components similarly demonstrated effective homogenization (FIG. 5b). Since drug half lives and dosing protocols for these combination therapies can generate concurrent presence of all four drugs in patients, a three drug CVA/CHO and a four-drug CVAD/CHOP signature were examined. Whereas a PCA plot with two principal components separated the four individual drugs into distinct quadrants (FIG. 3c), the sequential plotting of signatures resulting from increasing combination complexity pushed the combination projections toward the loci of the respective drug substituents until the four-drug combination of CVAD reached the origin—i.e., an essentially average signature. This four drug combination fit an averaging model, as did the two drug and three drug components of CVAD tested (FIG. 5b). Taken together, these data suggest that combination therapies can homogenize extant single-agent genetic dependencies.

Since the shRNA signatures revealed an averaging mechanism in response to CVAD, genetic dependencies were modeled even more explicitly. It was asked whether spontaneous heterogeneity in drug effectiveness evolving in individual mice during tumorigenesis (characterizing patient-to-patient variability) is diminished by combination therapy (FIG. 3d). When independent Eµ-Myc primary tumor lines were examined for single versus combination drug effects in vitro, different primary lymphomas displayed distinct patterns of sensitivity or resistance to CVAD component drugs (FIGS. 3e and 3f, top). PCA analysis was again employed, now considering the tumor lines as variables analogously to the shRNAs previously. Examining each cell line's contribution to principal components 1 and 2 (FIGS. 3e and f), it was found that individual cell line behaviors were more diverse following treatment with single agents, as evidenced by the higher variance requiring multiple principal components to explain. This complexity was diminished in the combination case, where principal component 1 could explain more than 93% of the cumulative variance. Thus, tumor-specific variation in the response to single agent treatment was homogenized in the presence of combination therapy.

Figure 4A:
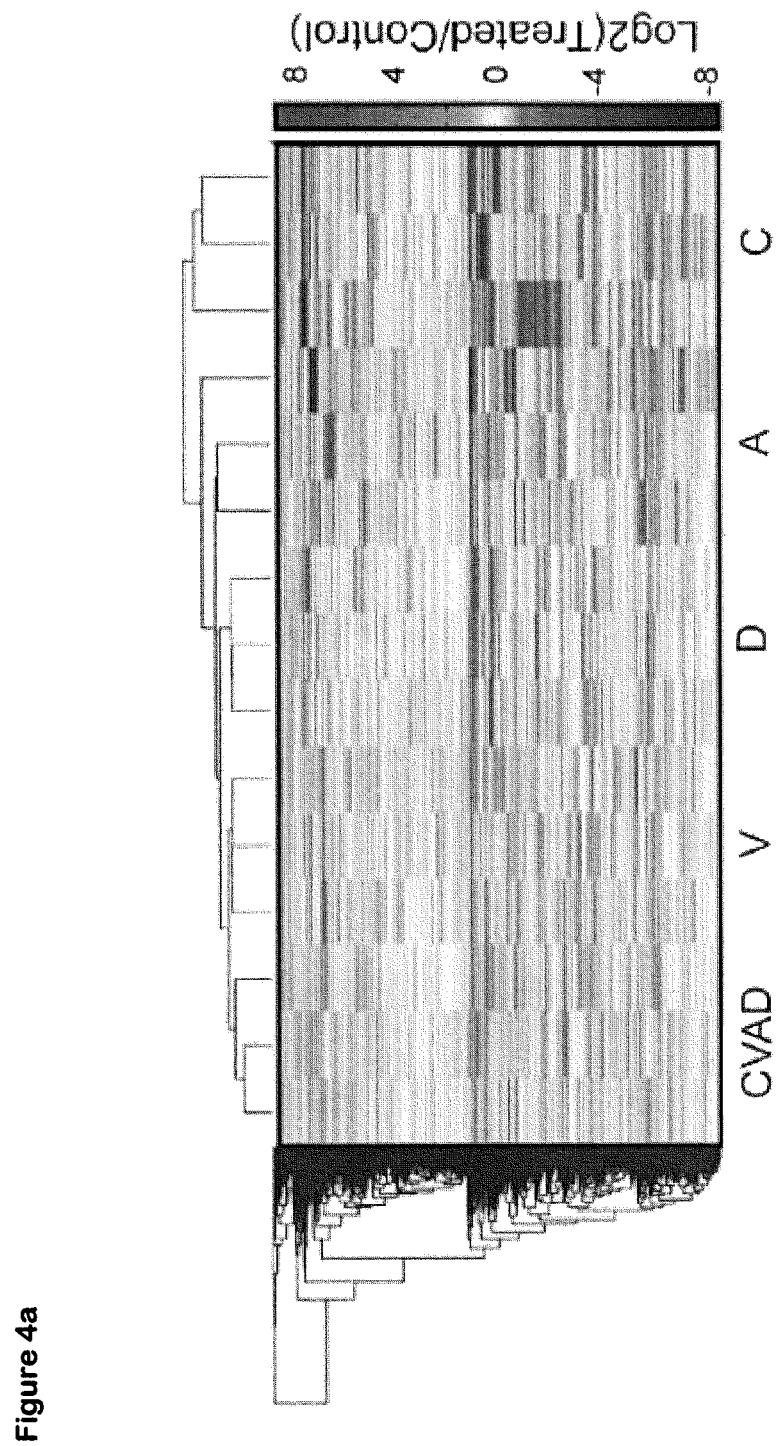
FIGS. 4a-4d: An unbiased screen suggests that CHOP/CVAD averages the phenotypes conferred by a diverse set of shRNAs. (4a) A clustergram of 6819 shRNAs that were well represented (>700 reads/sequencing lane) for biological replicates of cells treated with the indicated drugs. (4b) A scatter plot of the data contained in A showing the average log enrichment across all drug biological replicates, versus the coefficient of variation. Each dot corresponds to one shRNA in one drug condition. This data was filtered according to a reproducibility and strength criterion (below), yielding 93 informative shRNAs. The CVAD shp53 data is indicated as a reference for the strength criterion in the distribution. (4c) A heatmap of the indicated enrichment or depletion data for the 93 shRNAs demonstrates the range of phenotypes and their similarity to an averaging model. (4d) Top: 7 of the 8 shRNAs in the 8-shRNA signature were contained among the filtered 6819 shRNAs. They are plotted as a scatter plot relative to the prediction of additivity. The line represents perfect model:data fit. Error bars depict the SEM. Bottom: The filtered 93 shRNAs are plotted as a scatter plot relative to the prediction of additivity. The line represents perfect model:data fit. The deviation from the model prediction (above) is used to produce a 0.05 significance threshold. The 15/93 that deviate are coded in red. Error bars depict the SEM.
Figure 4B:
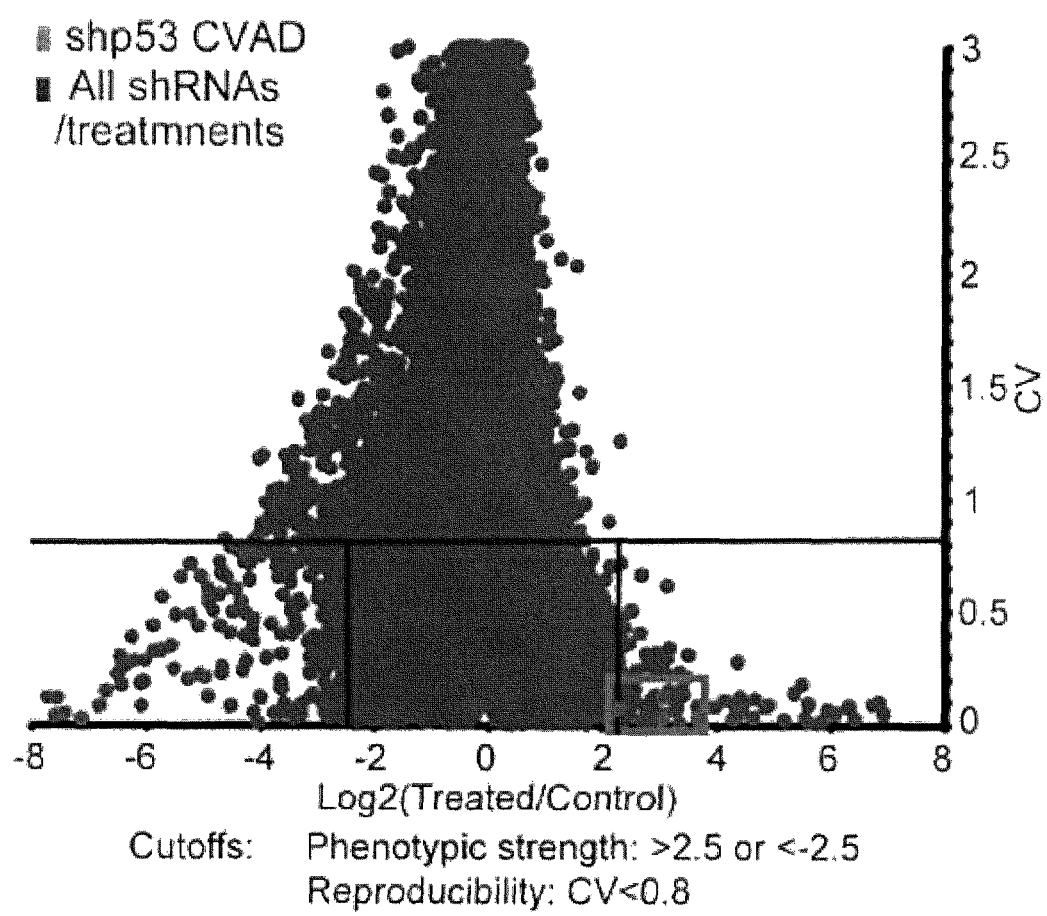
Figure 4C:
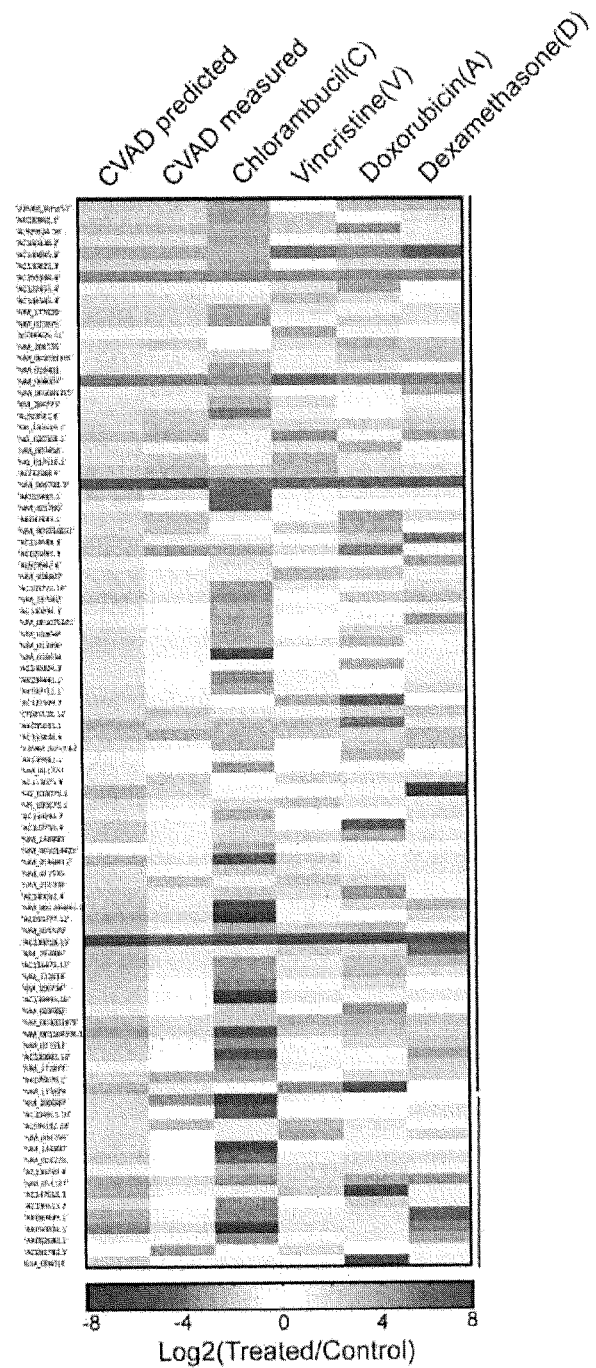
Figure 4D:
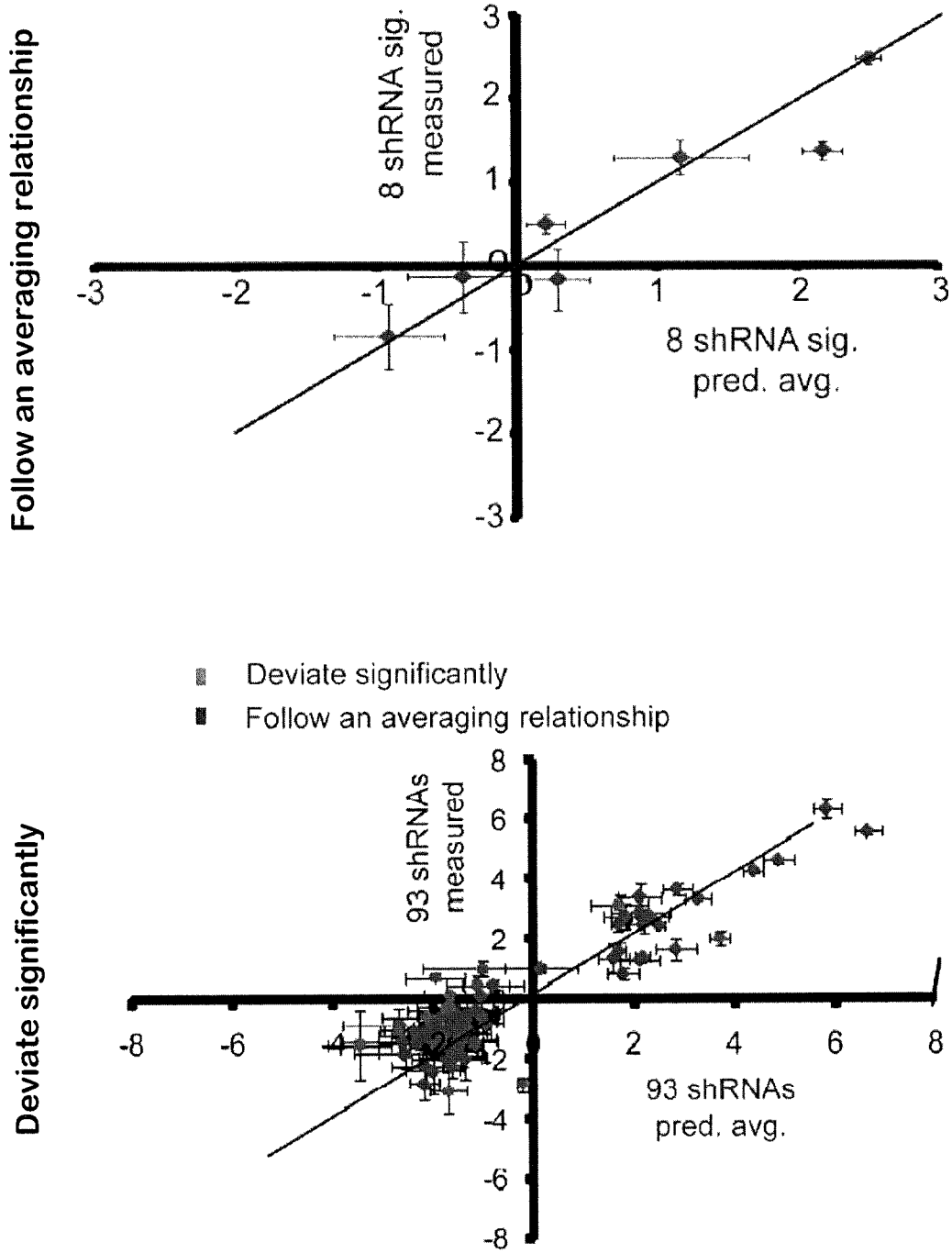
Figure 6:
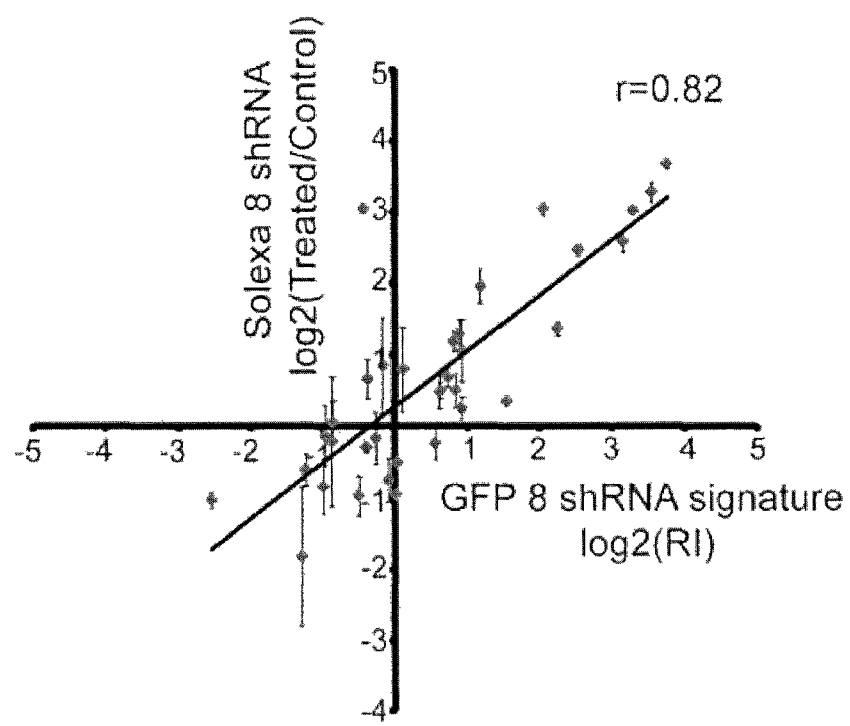
FIG. 6: Pooled Solexa sequencing measurements of 7 of the 8 shRNA (filtered >700 reads) signature hairpins are plotted relative to their 72 hour GFP enrichment scores for C, V, A, D, and CVAD dosings. r is the pearson correlation coefficient between the two measurements.
Figure 7:
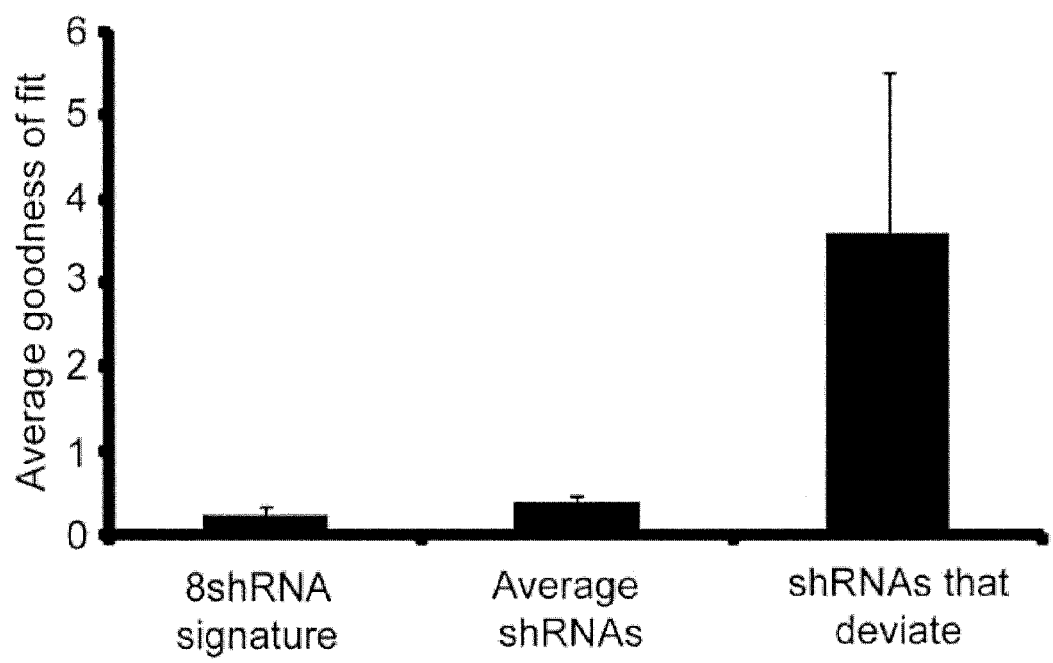
FIG. 7: The average fit to an averaging model for the solexa 8 shRNA signature date, the 78 hairpins that appear to be averages and the 15 hairpins that do not.

Given the extraordinary number of genetic and epigenetic changes typically present in human tumors, the broader relevance of this averaging effect was further validated. A pooled, partial genome scale screen of a randomly selected set of 10,000 shRNAs, in which the 8 shRNA signature was added at a 1:10,000 ratio as an internal control, was preformed. Single agent C, V, A, D were compared to combination CVAD/CHOP for each shRNA in the pooled set. Of the initial pool, 6819 shRNAs (including 7 out of 8 of the 8 shRNA signature) were present at high enough abundance (>700 sequencing reads per shRNA) to be included in further analysis. To examine the robustness of this data set, it was first confirmed that the 3 biological replicates of drug treatments clustered together (FIG. 4a). Furthermore, representation of the 7/8 shRNAs from the 8-shRNA signature that were above the read number cutoff strongly correlated with single hairpin measurements (FIG. 6). As a more stringent data threshold, shRNAs were further filtered based on the magnitude of shRNA enrichment and the reproducibility of the sequencing data (FIG. 4b). This filter reduced the set of 6819 shRNAs to 93 putative shRNA "hits" that exhibited large and reproducible phenotypes (FIG. 4c). Whether these 93 shRNAs exhibited a genetic averaging mechanism following treatment with combination therapy was next examined. Using a cutoff of 2 standard deviations away from the control shRNAs, it was found that 78/93 shRNAs produced an average of individual drug phenotypes when treated with CVAD (FIG. 4d and FIG. 7). Moreover, the majority of shRNAs that deviated from this average (12/15) were "over-neutralized", meaning that these RNAs affected the response to combination therapy even less than the averaging mechanism predicts. Therefore most shRNA phenotypes were homogenized by the combination of CHOP/CVAD. This indicates that the vast majority of genetic dependencies (as modeled by shRNAs) are averaged in response to combination therapy.

Combination therapies are typically assumed to work by enhancing the tolerated cumulative drug dose or providing cell-intrinsic drug synergy. However, as shown herein, the most synergistic drug combinations examined are not widely used, and the standard cytotoxic chemotherapies used in lymphomas are not particularly synergistic. Therefore, while tolerable dose escalation (with non-overlapping toxicity) is certainly one important rationale for combination therapy (Frei, E., 3rd. Cancer research 45, 6523-6537 (1985); Frei, E., 3rd, et al., Clinical Cancer Research 4, 2027-2037 (1998)), the broad use of these combinations likely relate to their propensity to neutralize heterogeneity in response across patient populations rather than to achieve maximal response in any individual. This basic mechanism of neutralization of both introduced and spontaneous variation likely represent an unintended consequence of clinical trial design. Genetically unstratified cohorts that are randomly assigned to experimental or control groups are often used to iteratively define combinations that perform better than the previous generation of treatment. While these regimens manifest some of the greatest success stories in decades of cancer research, the lack of relevant molecular information during their inception has served to shape regimens that are broadly useful across myriad diverse patients rather than tailored to "driving" cancer lesions. An unintended consequence of population-based drug optimization is that the response to highly synergistic combinations that act to promote single drug mechanisms of action would vary significantly among patients. Thus, synergistic combinations might fail in clinical trials using unstratified patient cohorts. These data indicate that current and future efforts to improve combination regimens, for broadly effective coverage as well as for personalized cohorts, will require a greater understanding of the genetic determinants of combination drug response.

| Gene | Gene Function | Gene ID | shRNA Target Sequences * |
|---|---|---|---|
| p53 | sequence-specific transcription factor, proapoptotic | 22059 | CCACTACAAGTACATGTGTAA (SEQ ID NO: 1) TGGAGAGTATTTCACCCTCAA (18%) (SEQ ID NO: 2) |

-continued

| Gene | Gene Function | Gene ID | shRNA Target Sequences * |
|---|---|---|---|
| ATM | DNA damage response, checkpoint signaling, DNA repair, phosphorylation of p53 | 11920 | CACGAAGTCCTCAATAATCTA (SEQ ID NO: 3) |
| Chk2 | DNA damage response, checkpoint signaling, DNA repair, phosphorylation of p53 | 50883 | CAGAAACACATAATCATTAAA (SEQ ID NO: 4) CACTTTCACTATGTAGAAATA (SEQ ID NO: 5) |
| ATR | DNA repair, DNA replication, phosphorylation of p53 | 245000 | ACCCATGTTCTTGACATTGAA (SEQ ID NO: 6) ACCTTTAATGAGTGTCTTAAA (SEQ ID NO: 7) |
| Chk1 | DNA repair, DNA replication, phosphorylation of p53 | 12649 | CAGGAATATTCTGATTGGAAA (SEQ ID NO: 8) AAGGGCTTGACCAATTATAAA (SEQ ID NO: 9) |
| Smg1 | nonsense-mediated mRNA decay, DNA damage response, checkpoint signaling, phosphorylation of p53 | 233789 | CAGGATAGCAATAAAGATGAA CAGGCTGCATTCAATAACTTA (SEQ ID NO: 10) |
| DNA-PKcs | DNA damage response, DNA repair phosphorylation of p53 | 19090 | CAGGCCTATACTTACAGTTAA CTCCAACATGTAGAGAACAAA (SEQ ID NO: 11) |
| JNK1 | DNA damage response, stress signaling, phosphorylation of p53 | 26419 | TCAGAGCATAACAAACTTAAA (SEQ ID NO: 12) |
| p38 | DNA damage response, checkpoint signaling, stress signaling, phosphorylation of p53 | 26416 | CAGGTCTTGTGTTTAGGTCAA (SEQ ID NO: 3) |
| A1 | Bcl-2 family gene, anti-apoptotic | 12044 | GGAAGATGGCTTCATAAAGAA (SEQ ID NO: 14) |
| Bclb | Bcl-2 family gene, anti-apoptotic | 12049 | AAGGAATCCCTTGAAACCTAA (SEQ ID NO: 15) |
| Bclw | Bcl-2 family gene, anti-apoptotic | 12050 | GGCTATAAGCTGAGGCAGAAG (SEQ ID NO: 16) |
| Bclx | Bcl-2 family gene, anti-apoptotic (long form), pro-apoptotic (short form) | 12048 | GGAGAGCGTTCAGTGATCTAA (SEQ ID NO: 17) (targets both long and short forms of Bclx) |
| Bad | Bcl-2 family gene, pro-apoptotic | 12015 | CGCGAGAAACGTGCTTTATAA (SEQ ID NO: 18) |
| Bak | Bcl-2 family gene, pro-apoptotic | 12018 | CCGGAACCTATGATTACTTGA (SEQ ID NO: 19) |
| Bax | Bcl-2 family gene, pro-apoptotic | 12028 | CCGCGTGGTTGCCCTCTTCTA (SEQ ID NO: 20) |
| Bid | Bcl-2 family gene, pro-apoptotic | 12122 | CACAGAAGATTCCATATCAAA (SEQ ID NO: 21) |
| Bik | Bcl-2 family gene, pro-apoptotic | 12124 | CCGGACAGGTGTCAGAGGTAT (SEQ ID NO: 22) TAGGAACAGAGAAATATGCAA (SEQ ID NO: 23) |
| Bim | Bcl-2 family gene, pro-apoptotic | 12125 | CACCCTCAAATGGTTATCTTA (22%) (SEQ ID NO: 24) |
| Bmf | Bcl-2 family gene, pro-apoptotic | 171543 | CGCAGAGCCCTGGCATCACAA (SEQ ID NO: 25) |
| Bnip3l | Bcl-2 family gene, pro-apoptotic | 12177 | GGTATCAGACTGGTCCAGTAG (SEQ ID NO: 26) |

-continued

| Gene | Gene Function | Gene ID | shRNA Target Sequences * |
|---|---|---|---|
| Bclg | Bcl-2 family gene, less defined | 66813 | TCCAAACAGCATAGAGTTCAA (SEQ ID NO: 27) CTGGCCTCTGTGACTGCTCTA (SEQ ID NO: 28) |
| Bok | Bcl-2 family gene, less defined | 51800 | TCGGTGTCCAGCCCTAGAGAA (25%) (SEQ ID NO: 29) |
| BPR | Bcl-2 family gene, less defined | 75736 | CCCAGCCTCTTCCGAGTTCTA (SEQ ID NO: 30) |
| Hrk | Bcl-2 family gene, pro-apoptotic | 12123 | CAGCAGGGAGTGTCTACTTTA (SEQ ID NO: 31) |
| Mil1 | Bcl-2 family gene, pro-apoptotic | 94044 | CCTGAAGAAGTGAAGAGCTTA (SEQ ID NO: 32) |
| Mule | Bcl-2 family gene, E3 ligase for Mcl-1 and p53 | 59026 | CCACCTCAGCTACTTCAAGTT (SEQ ID NO: 33) |
| Noxa | Bcl-2 family gene, pro-apoptotic | 58801 | CAGATTGAATAGTATGTGATA (SEQ ID NO: 34) |
| Puma | Bcl-2 family gene, pro-apoptotic | 170770 | CTGTAGATATACTGGAATGAA (SEQ ID NO: 35) |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

---

What is claimed is:

1. A method of characterizing a mechanism of action of a combination of agents comprising:
   a) contacting each of eight populations of cells with a combination of agents to be assessed, wherein each population of cells expresses a small hairpin RNA (shRNA) that targets one of eight genes present in the cells, said eight genes consisting of p53, ATR, Chk1, Chk2, Smg-1, DNA-PKcs, Bok, and Bim genes; and
   b) determining a responsiveness of each of the eight populations of cells to the combination of agents to obtain a combined shRNA signature of the combination of agents for the eight populations of cells, thereby characterizing the mechanism of action of the combination of agents.

2. The method of claim 1 wherein the mechanism of action indicates that the combination of agents has a neutralizing effect, a synergistic effect, a novel effect or a similar effect when compared to effects of individual agents of the combination.

3. The method of claim 1 wherein the mechanism of action of the combination of agents comprises inhibition of a topoisomerase, cross linking of DNA, inducement of single stand break of DNA, inhibition of nucleic acid synthesis, inhibition of mitosis, inhibition of RNA transcription, inhibition of histone modification enzymes, inhibition of heat shock proteins, alkylation of DNA, or inhibition of proteasomes inducement of apoptosis.

4. The method of claim 1 further comprising classifying the combination of agents within a group of one or more agents or a combination of agents having in common one or more mechanisms of action.

5. The method of claim 1 wherein each shRNA acts to knock down the gene that it targets.

6. The method of claim 1 wherein the combination of agents is used in an effective amount to induce a response in cells that do not contain shRNA targeting any of said eight genes.

7. The method of claim 1 wherein the cells are mammalian cells.

8. The method of claim 1 wherein the responsiveness of each of the populations of cells to the combination of agents is a relative level of chemo-resistance and sensitization conferred by each shRNA.

9. The method of claim 1 wherein the responsiveness of each of the populations of cells is a relative survival rate compared to control cells that do not contain shRNA targeting any of the eight genes.

10. The method of claim 1 wherein each of the populations of cells further expresses a marker gene.

11. The method of claim 1 wherein the shRNAs are introduced into the cells using a viral vector.

12. The method of claim 11 wherein the shRNAs are introduced into the cells using a retroviral vector.

13. The method of claim 11 wherein the vector further expresses a marker gene.

14. The method of claim 10 wherein the marker gene is a fluorescent marker gene.

15. The method of claim 10 wherein the marker gene is green fluorescent protein (GFP) gene.

16. The method of claim 14 further comprising measuring the fluorescent marker gene or GFP gene expression level in each of the populations of cells using cell flow cytometry.

17. The method of claim 1 further comprising comparing the responsiveness of each of the populations of cells to the combination of agents to a control.

18. The method of claim 17 wherein the control is a population of cells into which no shRNA targeting any of the eight genes has been introduced.

19. The method of claim 1 wherein the determination of the responsiveness is accomplished using cell flow cytometry, hybridization techniques or sequencing techniques.

20. The method of claim 1 wherein each of the populations of cells are contacted with the combination of agents for about 1 hour, 4 hours, 8 hours, 12 hours, 16 hours, 20 hours, 24 hours, 28 hours, 32 hours, 36 hours, 40 hours, 44 hours, 48 hours, 52 hours, 56 hours, 60 hours, 64 hours, 68 hours, 72 hours, 76 hours, 80 hours, 84 hours, 88 hours, 92 hours, 96 hours, 100 hours or longer.

21. The method of claim 1 wherein each of the populations of cells is contacted repeatedly with the combination of agents.

22. The method of claim 1 further comprising introducing the shRNAs into each of the populations of cells.

23. The method of claim 1 further comprising, using a processor, clustering representations of a plurality of combinations of agents into groups based on the responsiveness of each of the populations of cells to each combination of agents.

24. The method of claim 23 wherein clustering the representations of the plurality of the combinations of agents into groups includes:
   determining an initial cluster size of a group of agents by determining an average of pairwise linkage distances among the group of agents, the group of agents formed based on the responsiveness of each of the populations of cells to each agent of the group;
   predicting whether the agent belongs to the group using a probabilistic nearest neighbor calculation between the agent and the group of agents; and
   if the agent is predicted to belong to the group, adding the agent to the group and determining a new cluster size for the group of agents, and determining a linkage ratio for the agent and the group of agents based on the initial cluster size and the new cluster size.

25. The method of claim 24 further comprising generating a background distribution of false linkage ratios by iteratively forcing out-of-group agents to belong to the group of agents.

26. The method of claim 25 wherein the background distribution indicates how unrelated agents affect cluster size.

27. The method of claim 25 further comprising comparing the new cluster size for the group of agents to the background distribution.

* * * * *